(12) United States Patent
Yoon et al.

(10) Patent No.: US 6,878,469 B2
(45) Date of Patent: Apr. 12, 2005

(54) MATERIAL FOR TRANSPORTING ELECTRONS AND ORGANIC ELECTROLUMINESCENT DISPLAY USING THE SAME

(75) Inventors: Seok-Hee Yoon, Daejeon (KR); Jae-Soon Bae, Daejeon (KR); Youn-Gu Lee, Seoul (KR); Sung-Gap Im, Daejeon (KR); Jae-Chol Lee, Daejeon (KR); Ji-Eun Kim, Daejeon (KR); Kong-Kyeom Kim, Daejeon (KR); Se-Hwan Son, Daejeon (KR); Young-Kyu Han, Daejeon (KR)

(73) Assignee: LG Chem, Ltd., Seoul (KR)

( * ) Notice: Subject to any disclaimer, the term of this patent is extended or adjusted under 35 U.S.C. 154(b) by 71 days.

(21) Appl. No.: 10/345,310

(22) Filed: Jan. 16, 2003

(65) Prior Publication Data

US 2003/0165715 A1 Sep. 4, 2003

(30) Foreign Application Priority Data

Jan. 18, 2002 (KR) .................................. 2002-0003025

(51) Int. Cl.⁷ ........................ H05B 33/12; C07D 209/02
(52) U.S. Cl. ........................ 428/690; 428/917; 313/504; 313/506; 548/304.4; 548/304.7; 548/310.7
(58) Field of Search ................................ 428/690, 917; 313/504, 506; 548/304.4, 304.7, 310.7

(56) References Cited

U.S. PATENT DOCUMENTS

| | | | |
|---|---|---|---|
| 4,356,429 A | 10/1982 | Tang ........................... | 313/503 |
| 4,539,507 A | 9/1985 | VanSlyke et al. ........... | 313/504 |
| 5,645,948 A | 7/1997 | Shi et al. .................... | 428/690 |
| 5,766,779 A | 6/1998 | Shi et al. .................... | 428/690 |
| 6,171,715 B1 * | 1/2001 | Sato et al. ................... | 428/690 |
| 6,436,558 B1 | 8/2002 | Sato et al. ................... | 428/690 |

FOREIGN PATENT DOCUMENTS

| | | |
|---|---|---|
| EP | 0 700 917 A2 | 3/1996 |
| JP | 57-51781 | 3/1982 |
| JP | 59-194393 | 11/1984 |
| JP | 1-245087 | 9/1989 |
| JP | 2-189890 | 7/1990 |
| JP | 2-222484 | 9/1990 |
| JP | 2-289675 | 11/1990 |
| JP | 3000791 | 1/1991 |
| JP | 3-33183 | 2/1991 |
| JP | 6-322362 | 11/1994 |
| JP | 11-345686 | 12/1999 |
| JP | 2000-113985 | 4/2000 |
| WO | WO 02/088274 A1 * | 11/2002 |

OTHER PUBLICATIONS

Pope et al., *The Journal of Chemical Physics*, vol. 42, No. 7, Apr. 1, 1965, pp. 2540–2543.
Tang et al., *Appl. Phys. Lett.*, vol. 51, No. 12, Sep. 21, 1987, pp. 913–915.
Helfrich et al., *Physical Review Letters*, vol. 14, No. 7, Feb. 15, 1965, pp. 229–231.

* cited by examiner

*Primary Examiner*—Marie Yamnitzky
(74) *Attorney, Agent, or Firm*—Birch, Stewart, Kolasch, & Birch, LLP

(57) ABSTRACT

Novel materials for electron injection/transportation and emitting layers can greatly improve the stability of an organic electroluminescent display. Electroluminescent displays incorporating these materials produce blue light at low voltage levels. These novel organic materials include compounds in which 1 to 2 imidazole functional groups are introduced in the 2 or 2,6-site of 9,10 substituted anthracene. An organic electroluminescent display with an organic compound layer of these materials has high efficiency, thermal stability, operationally stability and maintains driving voltage before and after operation.

37 Claims, 4 Drawing Sheets

MATERIAL FOR TRANSPORTING ELECTRONS AND ORGANIC ELECTROLUMINESCENT DISPLAY USING THE SAME

This application claims priority of Korean Patent Application No. 2002-0003025, filed Jan. 18, 2002, the entire content of which is hereby incorporated by reference.

BACKGROUND OF THE INVENTION

1. Field of the Invention

The present invention relates to a novel material for electron transportation and emitting layers, and an organic electroluminescent display using the same.

2. Description of the Related Art

An electroluminescent display is a luminescent device using electroluminescence of a solid fluorescent material. Current practical technology uses an inorganic electroluminescent display with an inorganic material as an illuminant. However, the conventional inorganic electroluminescent display requires a high voltage of 100 V or more for luminescence, and it is difficult for it to emit blue light. As a result, full colorization by the three colors of RGB (red, green, blue) is difficult.

Although studies of electroluminescent devices using organic materials have attracted attention for a long time, only a small number of devices have been commercialized due to their lack of stability and low efficiency compared to conventional display devices such as liquid crystal displays and cathode ray tubes. Organic electroluminescent displays are based on the theory that electrons and holes injected into an organic thin film of small molecules (sublimable molecules) or a polymer by way of an anode and a cathode form an exciton, and light with a specific wavelength is generated when the high-energy exciton returns to its ground states. This effect was first discovered with a single crystal of anthracene by Pope, et al. in 1965 (M. Pope et al., *J. Chem. Phys.*, 42, 2540, 1965). In 1987, an organic electroluminescent display with a laminated structure of a function-separation type dividing organic material into a hole transporting layer and a emitting layer was suggested by Tang, from Kodak Company, and it has been confirmed that low voltage of 10 V or less and high luminance can be obtained (Tang, C. W.; VanSlyke, S. A. *Appl. Phys. Lett.* 1987, 51, 913). Since then, organic electroluminescent displays began to attract attention. At present, studies of organic electroluminescent displays with this same function-separation type laminated structure are progressing.

The structure of a conventional organic electroluminescent display contains, as shown in FIG. 1, a substrate (1), an anode (2), a hole injection layer (3) for receiving holes from the anode, a hole transportation layer (4) for transporting holes, an emitting layer (5) in which holes and electrons are bound to emit light, an electron transportation layer (6) for receiving electrons from a cathode to transfer them to the emitting layer, and a cathode (7). The emitting layer (5) can be composed of two or more different molecules to further increase the device efficiency by separating the roles of light emission and transporting both electrons and holes. Generally, the molecule transporting both holes and electrons is called a host molecule and the other molecule emitting light is called a dopant molecule. Usually, the emitting layer (5) is composed of a majority of host molecules and small amounts (1 to 20%) of dopant molecules. The requirements of a dopant molecule include high fluorescent or phosphorescent efficiency with proper band structure relative to the host molecule. According to the circumstances, a small amount of fluorescent or phosphorescent dye is doped on the electron transportation layer (6) or on the hole transportation layer (4) to comprise an emitting layer therein without a separate emitting layer (5). Also it is possible to dope more than one layer such as electron transporting, emitting and hole transporting layers to improve the operational stability or to have multiple emissions. Organic thin films between two electrodes are formed by vacuum deposition, spin coating, ink jet printing, roll coating, etc. For efficient injection of electrons from the cathode, a separate electron injection layer is often inserted.

The reason for manufacturing an organic electroluminescent display with a multi-layered thin film structure includes stabilization of the interfaces between the electrodes and the organic layers. In addition, in organic materials, the mobility of electrons and holes significantly differ, and thus, if appropriate hole transportation and electron transportation layers are used, holes and electrons can be efficiently transferred to the luminescent layer. Also, if the density of the holes and electrons are balanced in the emitting layer, luminescence efficiency can increase.

The proper combination of organic layers described above can enhance the device efficiency and lifetime. However, it has been very difficult to find an organic material that satisfies all the requirements for use in practical devices. For example, tris-(8-hydroxyquinoline) aluminum (Alq3) has been used as an electron transport material for more than 15 years, and there have been many publications and patents claiming they have superior properties. Therefore, it is crucial to find a molecule that has superior properties compared to the conventional material in all practical aspects, such as high efficiency, thermal stability, operational stability and maintaining the driving voltage before and after operation.

SUMMARY OF THE INVENTION

The invention is made in consideration and is directed at overcoming the problems of the conventional art electroluminescent displays. An object of the invention, in part, is to provide a novel material for electron transport and emitting layers that can largely improve luminescence efficiency, stability, and display lifetime of an organic electroluminescent display using the same.

The invention, in part, provides a compound represented by Chemical Formula 1, a compound represented by Chemical Formula 2, a compound represented by Chemical Formula 3, a compound represented by Chemical Formula 4, and a compound represented by Chemical Formula 5:

(Chemical Formula 1)

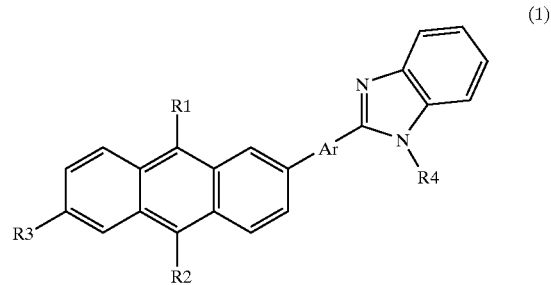

(1)

(Chemical Formula 2)

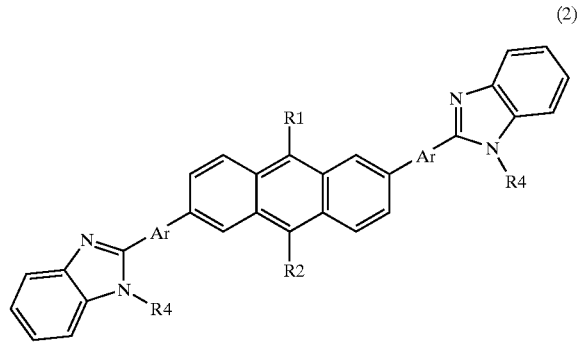

(2)

(Chemical Formula 3)

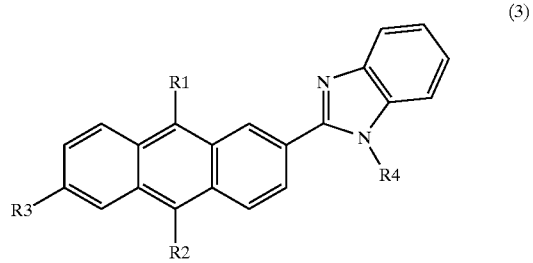

(3)

(Chemical Formula 4)

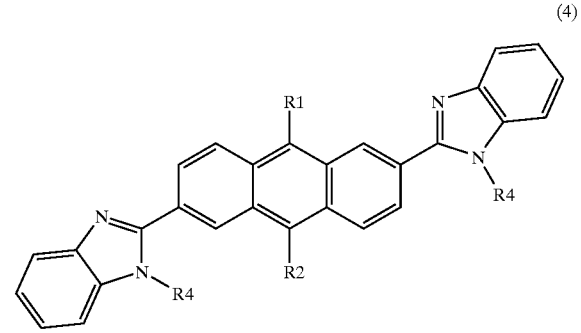

(4)

(Chemical Formula 5)

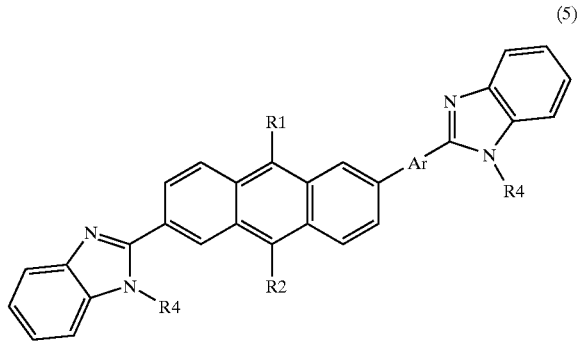

(5)

wherein
$R^1$ and $R^2$ are independently or simultaneously a hydrogen atom, a $C_{1-20}$ aliphatic hydrocarbon, benzene, naphthalene, biphenyl, anthracene, or a group derived from an aromatic heterocycle or an aromatic ring, and $R^1$ and $R^2$ cannot simultaneously be hydrogen atoms;

Ar is benzene, naphthalene, biphenyl, anthracene, or a group derived from an aromatic heterocycle or an aromatic ring;

$R^3$ is a hydrogen atom, a $C_{1-20}$ alkyl or aliphatic hydrocarbon, a substituted or unsubstituted benzene, naphthalene, biphenyl, anthracene, or an aromatic heterocycle or aromatic ring;

$R^4$ is a hydrogen atom, a $C_{1-12}$ alkyl or aliphatic hydrocarbon, benzene, naphthalene, biphenyl, anthracene, or a group derived from an aromatic heterocycle or aromatic ring.

The invention, in part, also provides an organic electroluminescent device having an organic layer containing an organic compound selected from compounds represented by the above Chemical Formula 1, Chemical Formula 2, Chemical Formula 3, Chemical Formula 4, or Chemical Formula 5, or a mixture thereof.

In the electroluminescent display of the invention, at least one of the organic layers can be located between an anode that injects holes and a cathode that injects electrons. Also, at least one of the organic layers can be an electron injection/transporting layer performing functions of electron injection and transportation. Further, at least one of the organic layers can be an electron injection/transporting and emitting layer performing functions of electron injection and luminescence. Yet further, at least one of the organic layers can be an electron transportation and emitting layer performing functions of electron transportation and light emission. Also, one of the organic layers can be an emitting layer performing the function of light emission.

The invention, in part, pertains to an organic electroluminescent display having a substrate, an anode over the substrate, a hole injection layer over the anode, a hole transportation layer over the hole injection layer, an emitting layer over the transportation layer, an electron transporting layer over the emitting layer and a cathode over the electron transporting layer; and the organic compound is contained in at least the emitting layer. Alternatively, the organic electroluminescent display has a substrate, an anode over the substrate, a hole injection layer over the anode, a hole transportation layer over the hole injection layer, an emitting layer over the hole transportation layer, an electron injecting/transporting layer over the emitting layer, and a cathode over the electron transportation layer; and the organic compound is contained in at least one of the electron injecting/transporting layer.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION

Advantages of the invention will become more apparent from the detailed description given herein after. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention provides a novel material in which 1 to 2 imidazole containing groups are introduced at 2 or 2,6-sites of 9,10 substituted anthracene. This material is contained in an organic compound layer of organic electroluminescent (EL) devices to improve luminescence efficiency and lifetime, and an organic electroluminescent devices comprising the same in an organic compound layer.

The structure of organic electroluminescent devices to which the novel material of the invention can be applied will be explained.

Figure 1:
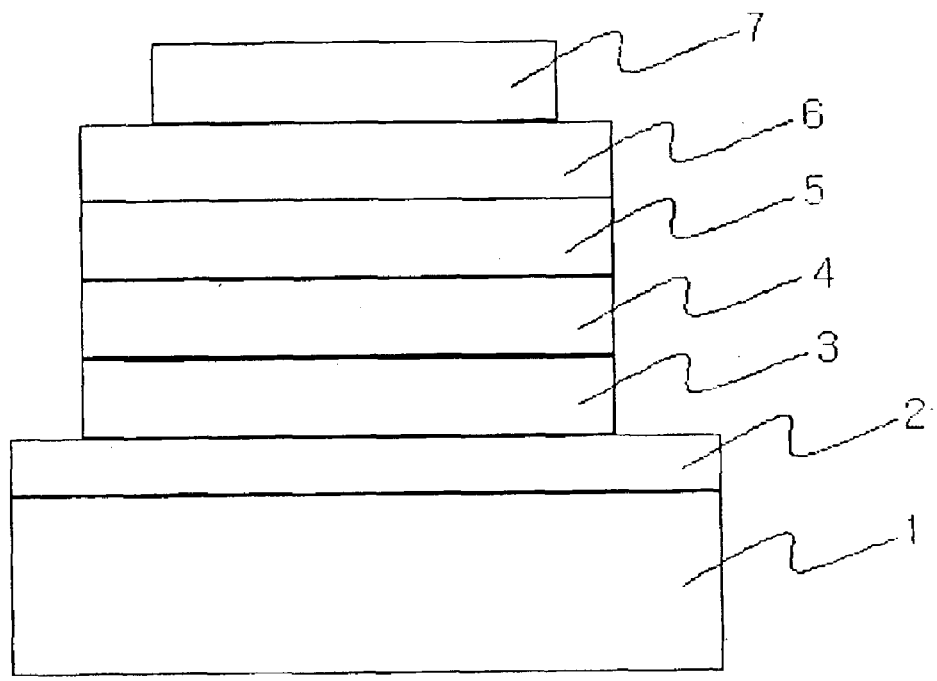
FIG. 1 is a cross sectional view showing an example of an organic electroluminescent display.

FIG. 1 is a cross-sectional view showing an example of the applicable structure of an organic electroluminescent display. Reference numeral 1 indicates a substrate, 2 an anode, 3 a hole injection layer, 4 a hole transportation layer, 5 an emitting layer, 6 an electron transportation layer, and 7 a cathode.

The substrate (1) supports of an organic electroluminescent device, and a silicon wafer, a quartz or glass plate, a metal plate, a plastic film or sheet, etc. can be used. Also, the substrate layer can be a thin protective layer on top of the anode when the device fabrication process starts from the cathode side.

On the substrate (1), an anode (2) is located. The anode (2) injects holes into a hole injection layer (3) located thereon. For this, a metal such as aluminum, gold, silver, nickel, palladium, platinum, etc., or a material with a large work function such as indium-tin oxide (ITO), indium-zinc oxide (IZO), etc. can be used, and a conductive polymer such as carbon black, polythiophene, polypyrrole, or polyaniline, etc. can also be used.

Over the anode (2), a hole injection layer (3) is located. Material for the hole injection layer (3) should have high hole injection efficiency from the anode and should efficiently transport injected holes. For this, the material should have a low ionization potential, high transparency to visible light rays and have superior stability for holes.

Over the hole injection layer (3), a hole transportation layer (4) is located. The hole transportation layer (4) receives holes from the hole injection layer (3) to transport them to an emitting layer (5) located thereon, and it also has a high hole transportation degree, stability for holes and blocks electrons well. In addition to these general requirements, if applied for a display for vehicles, heat resistance of the display is required, and a material having a glass transition temperature (Tg) over 70° C. is preferable. Materials satisfying these requirements include NPD (or NPB) (N',N-di(1-naphthyl)-N,N'-diphenyl-1,1'-diphenyl-4-4'diamine), spiro-arylamine compounds, perylene-arylamine compounds, azacycloheptatriene compounds, bis(diphenylvinylphenyl)anthracene, silicon-germanium oxide compounds, silicon arylamine compounds, etc.

Over the hole transportation layer (4), an emitting layer (5) is located. In the emitting layer (5), holes and electrons respectively injected from the anode (2) and a cathode (7) recombine to emit light, and the emitting layer (5) is formed from a material with high quantum efficiency. To make a stable device, it is crucial to have an emitting material which is stable to both holes and electrons. If the emitting material lacks stability to one of the carriers (either a hole or an electron), it is necessary to provide special circumstances for the emitting material not to be exposed to the carrier, which can deteriorate the emitting material. One method to evade such a condition is to dope a fluorescent or phosphorescent material that can accept and transport the problematic carriers instead of the host material. Another method is to introduce an excessive amount of the opposite carrier to minimize the chance of having the problematic carrier to attack the neutral host material. Therefore, it is very difficult to produce such conditions while maintaining optimum balancing of both carriers and introducing the proper amount of dopant material to maximize the quantum efficiency. Also, the choice of dopants capable of producing such a condition would be limited. For this reason, it is very important to have emitting material having stabilities to both carriers.

Materials used for emitting layers include, for green, Alq3; and for blue, Balq (8-hydroxyquinoline beryllium salt), DPVBi (4,4'-bis(2.2-diphenylethyenyl)-1,1'-biphenyl), spiro-DPVBi (spiro-4,4'-bis(2,2-diphenylethyenyl)1,1'-biphenyl), LiPBO (2-2(-benzoxazoyl)-phenol lithium salt), aluminum-quinoline metal complexes, derivatives of imidazole, thiazole, and oxazole and also their metal complexes, etc. In order to increase blue luminescence efficiency, a small amount of perylene and BczVBi (3,3'[(1, 1'-biphenyl)-4,4'-diyldi-2,1-ethenediyl]bis(9-ethyl)-9H-carbazole, or DSA (distrylamine), can be doped therein. For red, a small amount of material such as DCJTB ([2-(1,1-dimethylethyl)-6-[2-(2,3,6,7-tetrahydro-1,1,7,7-tetramethyl-1H,5H-benzo(l,j)quinolizin-9-yl)ethenyl]4H-pyran-4-ylidene]-propanedinitrile) is doped on green emitting material. If the emitting layer is formed by a process such as ink jet printing, roll coating, spin coating, etc., a polyphenevinylene (PPV) polymer or polyfluorene, etc. can be used for the emitting layer (5).

An electron transportation layer (6) is located over the emitting layer (5). The electron transportation layer (6) requires a material that has a high electron injection efficiency from a cathode (7) located thereon and that can efficiently transport the injected electrons. For this, it should be made of a material having a high electron affinity and mobility and superior stability for electrons. Also, the electron transportation layer (6) requires stable interface formation with the cathode material, otherwise delamination of the cathode layer and inefficient electron injection during operation occurs, resulting in a significant voltage increase. A voltage increase due to inefficient electron injection makes the display device less efficient and requires more power consumption. Also, it has been known that doping of the electron transportation layer with conductive metals having low work-functions enhances the electron injection from the cathode and forms a stable interface with metallic cathode layers. Materials used for the electron transportation layer include aromatic compounds such as tetraphenyl butadiene, etc. (Japanese Laid Open Patent Publication No. Sho 57-51781); metal complexes such as 8-hydroxyquinoline, etc. (Japanese Laid Open Patent Publication No. Sho 59-194393); metal complexes of 10-hydroxy benzo[h] quinoline (Japanese Laid Open Patent Publication No. Hei 6-322362); cyclopentadiene derivatives (Japanese Laid Open Patent Publication No. Hei 2-289675); bis styryl benzene derivatives (Japanese Laid Open Patent Publication No. Hei 1-245087 and Japanese Laid Open Patent Publication No. Hei 2-222484); perylene derivatives (Japanese Laid Open Patent Publication No. Hei 2-189890 and Japanese Laid Open Patent Publication No. Hei 3-791); p-phenylene derivatives (Japanese Laid Open Patent Publication No. Hei 3-33183); imidazole derivatives (U.S. Pat. No. 5,766,779); and oxazole derivatives (Japanese Laid Open Patent Publication No. Hei 11-345686), etc.

A cathode (7) is located over the electron transportation layer (6). The cathode (7) injects electrons into the electron transportation layer (6). As materials for the cathode, a metal having a low work function is preferable. Particularly, an appropriate metal such as tin, magnesium, indium, calcium, sodium, lithium, aluminum, silver, etc., or an appropriate alloy thereof can be used. Additionally, an electrode with a double-layered structure such as lithium fluoride and aluminum, lithium oxide and aluminum, strontium oxide and aluminum, etc. can be used. Although aluminum is known to have a work function of 4.2 eV, which is not low enough for efficient electron injection, a thin layer of insulating material enhances the electron injection by tunneling effect. Also, it is possible to co-deposit the cathodic metals with the electron transporting layer to enhance interfacial strength and electron injection.

The four layer organic structure located between opposite electrodes, exemplified above, can be altered. Adding more organic layers such as a hole-blocking or an electron blocking layer can improve the performance of the organic electroluminescence devices. Also, using less than four layers can simplify device structure.

Accordingly, at least one organic compound layer comprising the organic compound represented by the above Chemical Formulas 1 to 5 of the invention is located between an anode and a cathode. As explained, the novel material of the invention is contained in an organic compound layer between an anode and a cathode, preferably an electron, transportation, and emitting layers, thereby largely improving efficiency and device lifetime of an organic electroluminescent device. Also, an organic electroluminescent device that lowers operation voltage and has superior stability can be provided. A suitable dopant can be added to the material used in the invention to simultaneously perform functions of the electron transportation layer and the emitting layer without a separate emitting layer.

Thus far, organic small molecules having imidazole groups, oxazole groups, and thiazole groups have been frequently reported as materials for electron injection and transportation layers. However, before such materials were reported as materials for electron transportation, it had already been reported in EP 0700917 A2 (Motorola Company) that metal complexes of such materials were applied for blue luminescent or blue-green luminescent layers of an organic electroluminescent display. Additionally, U.S. Pat. Nos. 5,766,779 and 5,645,948 discuss organic electroluminescent displays in which organic materials having imidazole, thiazole, or oxazole groups are used for electron transportation layers and luminescent layers. According to U.S. Pat. No. 5,766,779, 2 to 8 of such hetero functional groups are contained in one molecule that was applied for an electron transportation layer of an organic electroluminescent device. In addition, U.S. Pat. No. 5,645,948 used an organic material comprising 3 to 8 of the same heterofunctional groups in one molecule applied for an emitting layer. In contrast, the invention has 1 to 2 heterofunctional groups are introduced at 2- or 2,6-positions of a 9,10-substituted anthracene moiety for use as a material for electron injection, transportation and light emitting layers.

TPBI (Chemical Formula 6) was introduced by Kodak Company in 1996 and discussed in U.S. Pat. Nos. 5,645,948 and 5,766,779 has been known as a representative material for electron transportation and blue emission. TPBI has an imidazole group, and as shown in the following Chemical Formula 6, it contains three N-phenyl benzimidazole groups in 1,3,5-substitution sites of benzene and performs functions for transporting electrons or as an emitting layer. However, in practical applications for displays, TPBI has lower operational stability as an electron transporting material as well as an emitting material than the material claimed in the invention, as is shown in the experimental parts the disclosure.

(Chemical Formula 6)

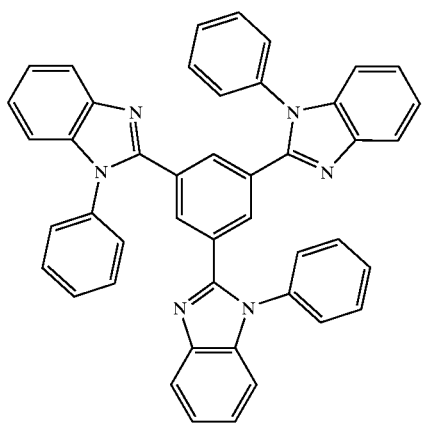

(6)

In addition, Japanese Laid Open Patent Publication Hei 11-345686 discusses a material for electron transportation disclosed in containing an oxazole group and a thiazole group as shown in the following Chemical Formulas 7 to 10, and it has been reported to be applicable for a luminescence layer. However, if put to practical use, it is not satisfactory in terms of operation voltage, brightness, and life cycle of a display.

(Chemical Formula 7)

(7)

(Chemical Formula 8)

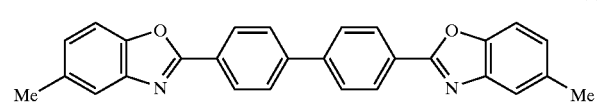

(8)

(Chemical Formula 9)

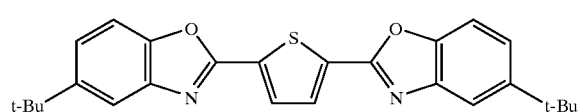

(9)

(Chemical Formula 10)

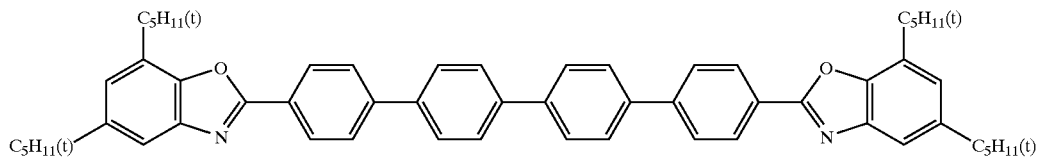

(10)

As seen from the conventional art, it had been understood that any organic material except an organometal complex such as Alq3 is difficult to practically use for a display. Thus, the present inventors synthesized a novel organic material represented by the above Chemical Formulas 1 to 5, selected appropriate hole injection and hole transportation, and emitting layers, and then applied it for electron injection and transportation layers. Therefore, they could obtain much superior results in terms of operation voltage, efficiency and lifetime of the display. Also, when the organic material represented by the above Chemical Formulas 1 to 5 is used as an emitting layer with a proper selection of hole injection, hole transportation and electron transporting layers, one could obtain an organic electroluminescent devices with superior operation voltage, and lifetime of the display The anthracene moiety used for novel emitting layers by the present inventors had been studied by Kodak Company, TDK, etc. in the U.S. and disclosed in various patents, but the historical origin of this anthracene technology had already begun in the early 1960's. Helfrich and Pope first announced the organic electroluminescence phenomenon using anthracene single crystals, but there was a lot of problems in practical use because the luminescence efficiency was low and a high voltage was required (W. Helfrich, W. G. Schneider, *Phys. Rev. Lett.* 14, 229, 1965. M. Pope, H. Kallmann, J. Giachino, *J. Chem. Phys.*, 42,2540, 1965).

Therefore, in order to develop an organic electroluminescent display having superior performance, it is very important which functional group is introduced at which site of the 10 reaction/substitution sites of anthracene. Most of the anthracene derivatives announced by Kodak Company and TDK, etc. are characterized by only being used for a luminescent layer of an organic electroluminescent device. Although anthracene derivatives disclosed in Japanese Laid Open Patent Publication No. Hei 11-345686 were asserted to be applicable for a luminescent layer and an electron transportation material, it was only included in the broad claims of the patent, and there was no mention in the Synthesis example or Examples, and so far there have been no examples for practically using it for electron injection and transportation materials.

In order to overcome these problems, the present inventors used the 2, 6, 9, 10 substitution sites of anthracene, while Japanese Laid Open Patent Publication No. Hei 11-345686 is characterized in that two substitution sites of 1 and 5, 1 and 8, or 2 and 6 were used, and the 9, 10 sites were substituted by hydrogen atoms.

The structural characteristics of the compounds represented by the above Chemical Formulas 1 to 5 synthesized by the present inventors are as follows. Anthracene has 10 substitution sites, and the present inventors focused on discovering an optimal compound while varying the four substitution sites of 2, 6, 9, 10 of anthracene, which is most characteristic in the present invention. Specifically, for 9, 10 sites of anthracene, aromatic hydrocarbons such as phenyl, naphthyl, biphenyl, etc. were independently or simultaneously substituted. For the 2 or 2,6 sites, imidazole groups were independently or simultaneously substituted, or aromatic hydrocarbons such as phenyl, etc. were substituted, and then imidazole groups were independently or simultaneously substituted to synthesize the material.

When the material is used for a layer having an electron transportation capacity in an organic electroluminescent display, operation voltage and life cycle of the display can be simultaneously improved. Representative materials will be explained in the following Examples in more detail. Representative materials of the present invention having electron transporting and emitting capacity are compounds of the following Chemical Formulas 1-1 to 1-10, Chemical Formulas 2-1 to 2-5, Chemical Formulas 3-1 to 3-5, Chemical Formulas 4-1 to 4-5, and Chemical Formulas 5-1 to 5-5.

(Chemical Formula 1-1)

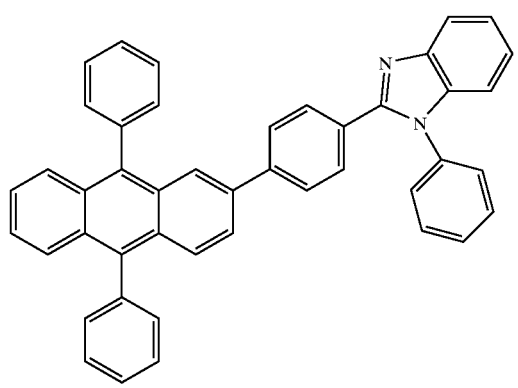

(1-1)

(Chemical Formula 1-2)

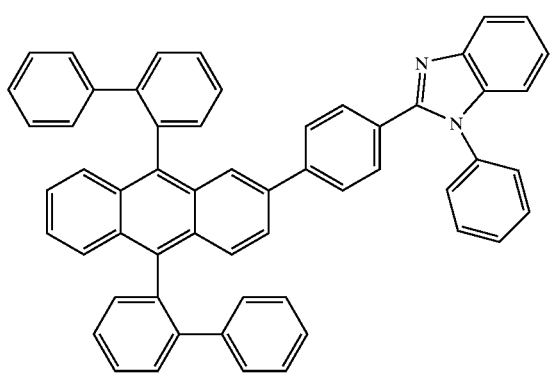

(1-2)

(Chemical Formula 1-3)
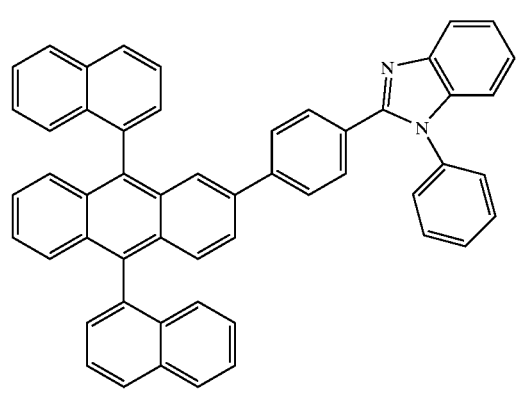
(1-3)
(Chemical Formula 1-4)
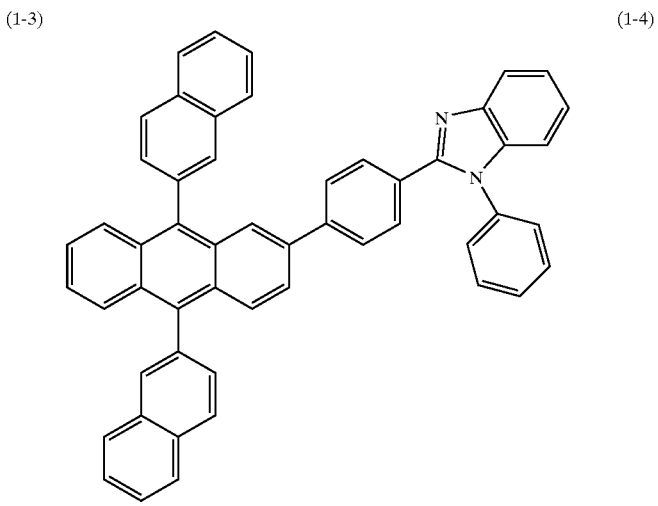
(1-4)
(Chemical Formula 1-5)
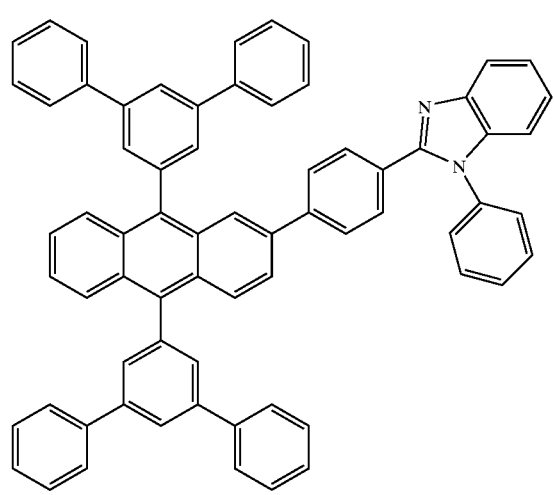
(1-5)
(Chemical Formula 1-6)
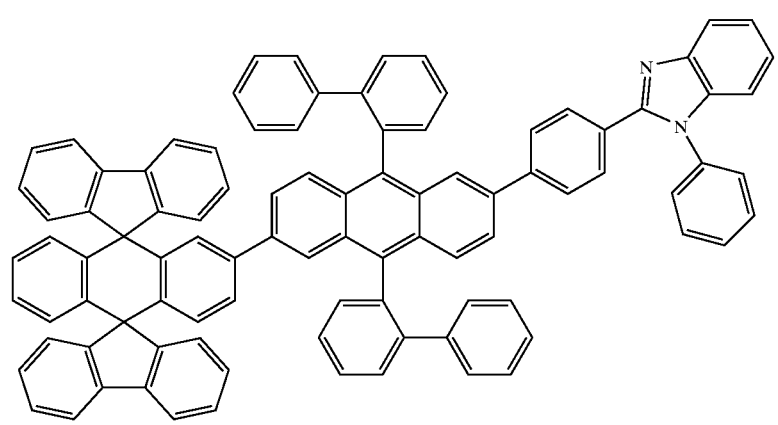
(1-6)

(Chemical Formula 1-7)
(1-7)
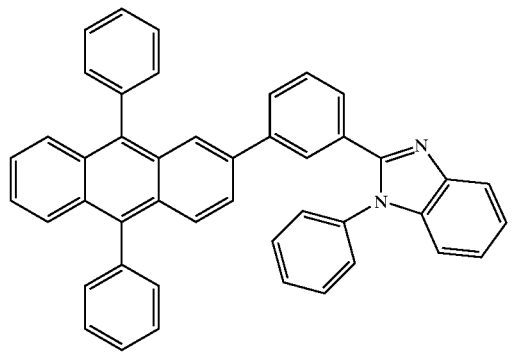
(Chemical Formula 1-8)
(1-8)
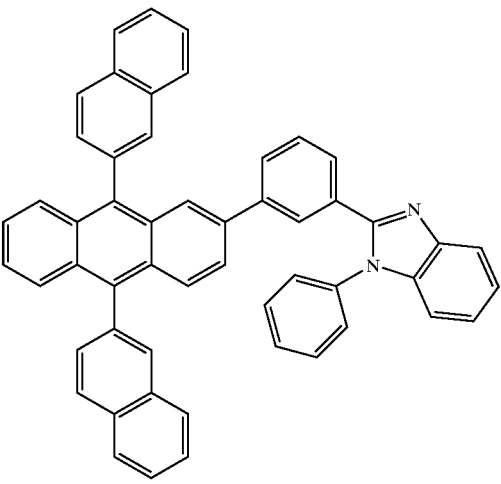
(Chemical Formula 1-9)
(1-9)
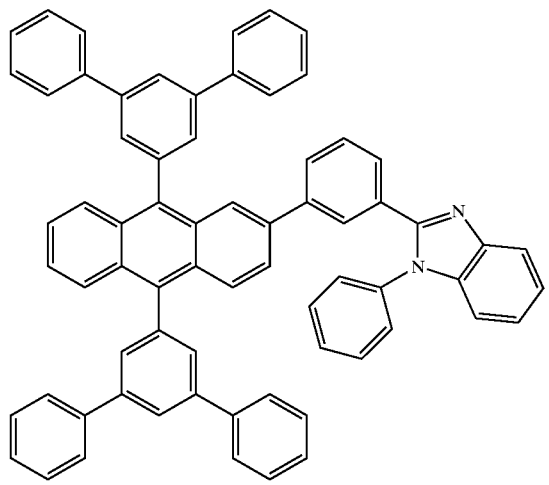
(Chemical Formula 1-10)
(1-10)
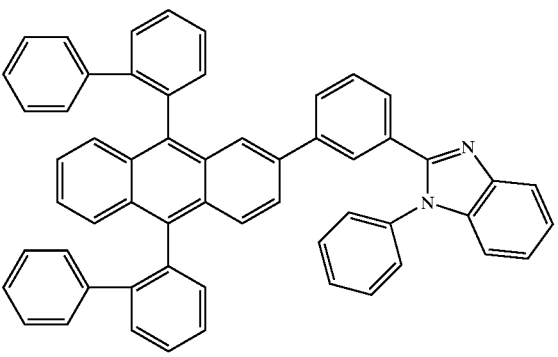
(Chemical Formula 2-1)
(2-1)
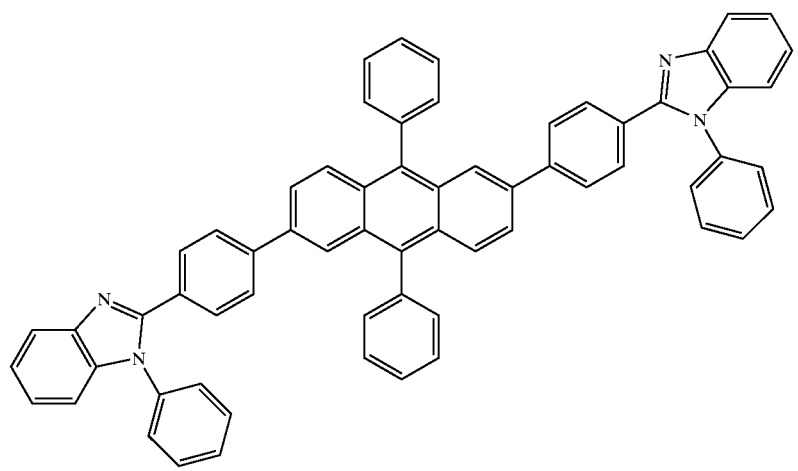

(Chemical Formula 2-2)
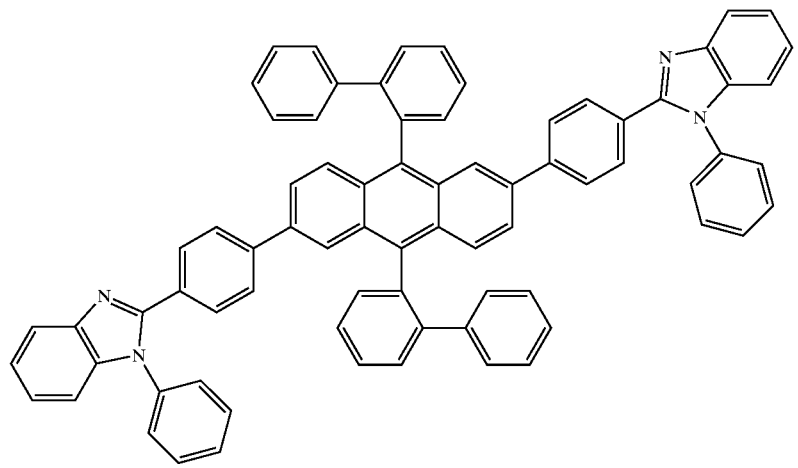
(2-2)
(Chemical Formula 2-3)
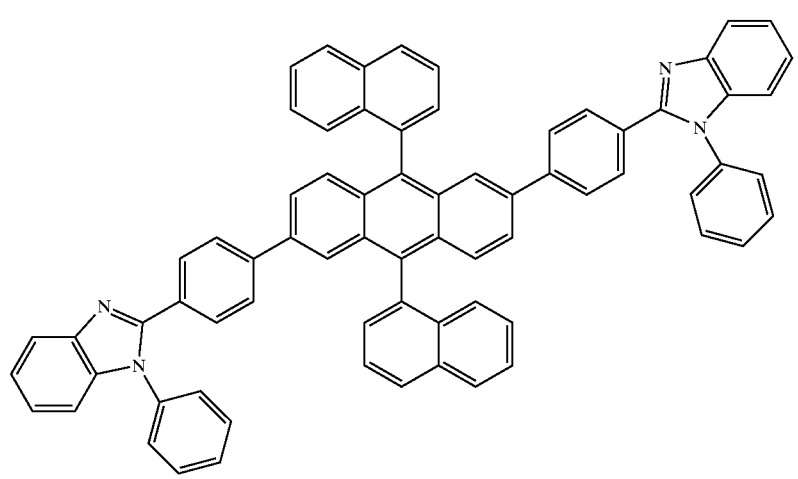
(2-3)
(Chemical Formula 2-4)
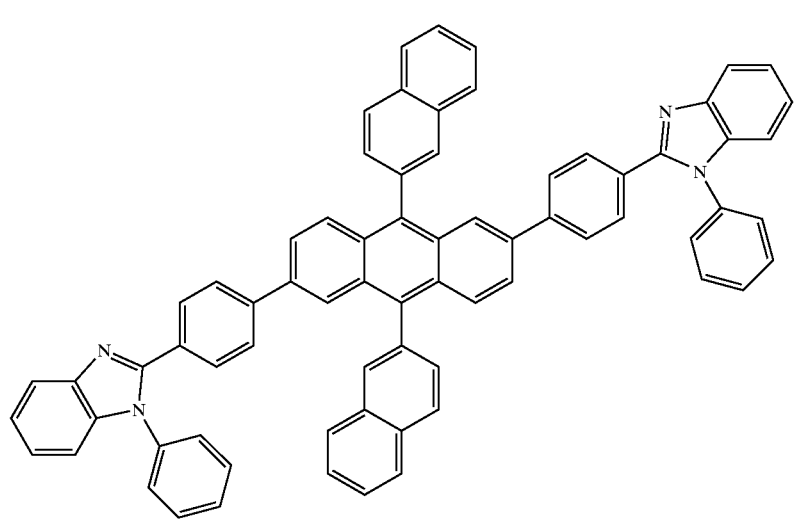
(2-4)

(Chemical Formula 2-5)
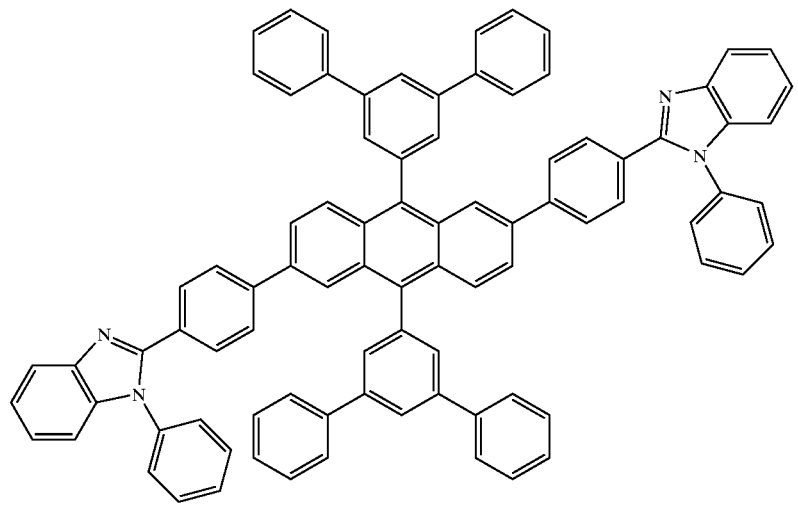
(2-5)
(Chemical Formula 3-1)
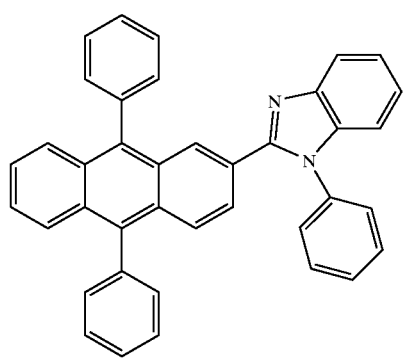
(3-1)
(Chemical Formula 3-2)
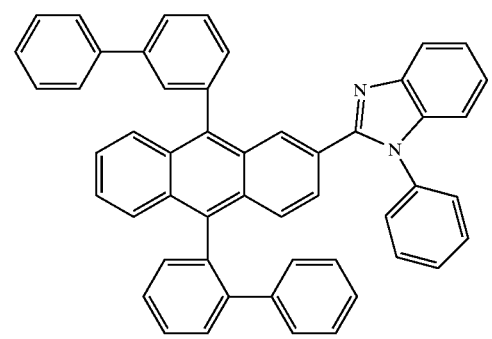
(3-2)
(Chemical Formula 3-3)
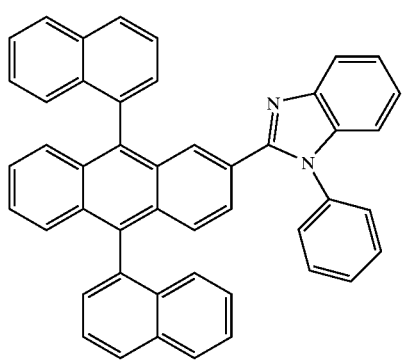
(3-3)
(Chemical Formula 3-4)
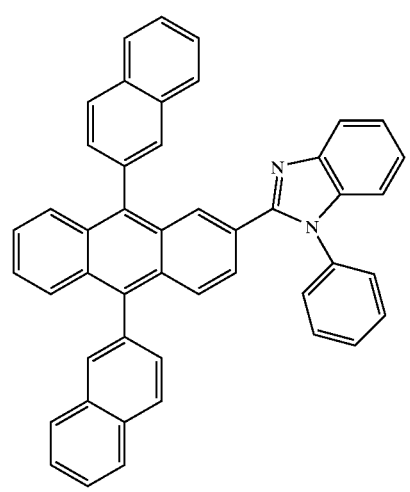
(3-4)

(Chemical Formula 3-5)
(3-5)
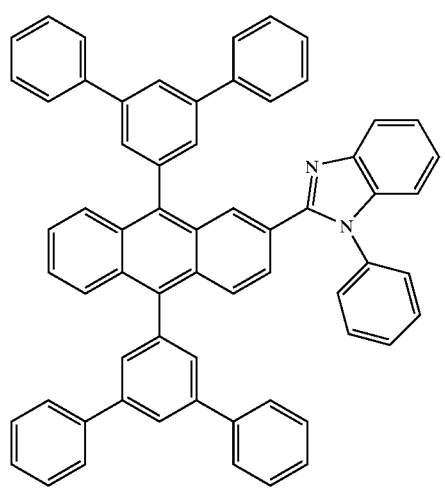
(Chemical Formula 4-1)
(4-1)
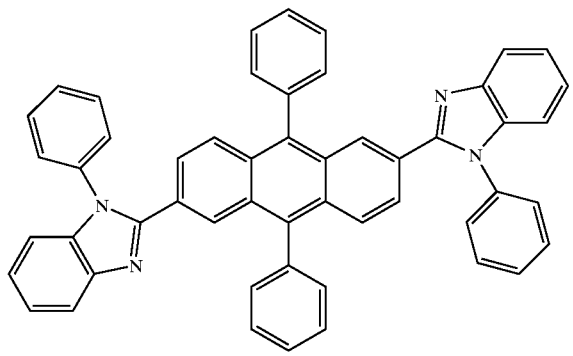
(Chemical Formula 4-2)
(4-2)
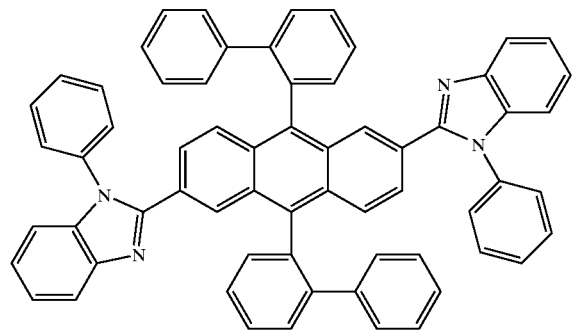
(Chemical Formula 4-3)
(4-3)
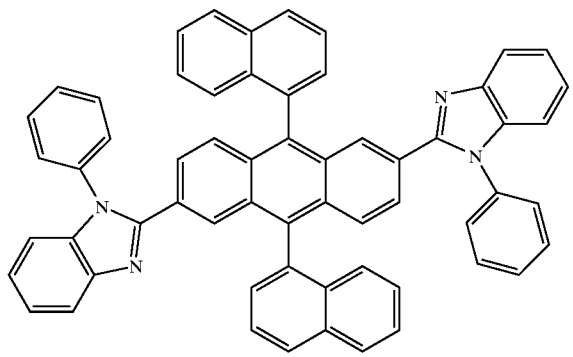
(Chemical Formula 4-4)
(4-4)
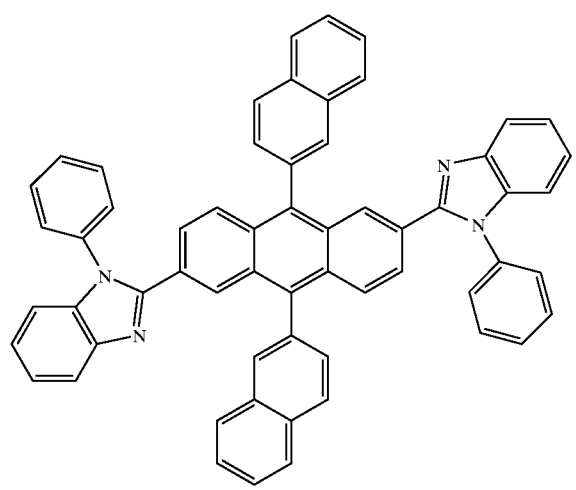
(Chemical Formula 4-5)
(4-5)
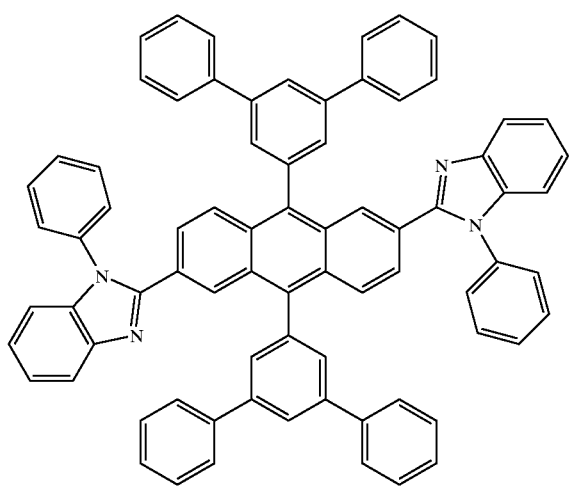

(Chemical Formula 5-1)

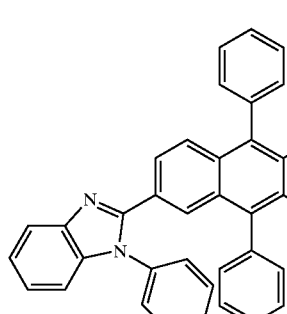

(5-1)

(Chemical Formula 5-2)

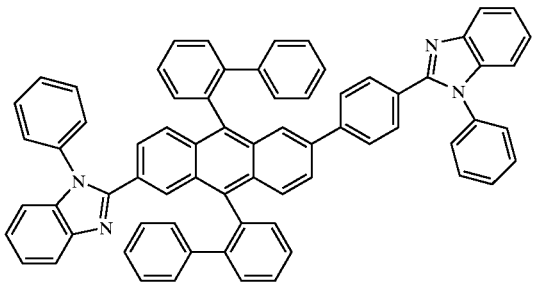

(5-2)

(Chemical Formula 5-3)

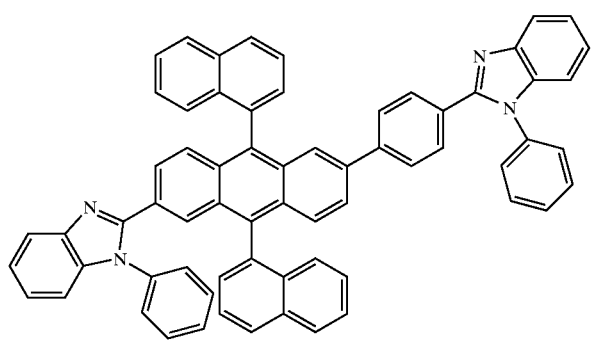

(5-3)

(Chemical Formula 5-4)

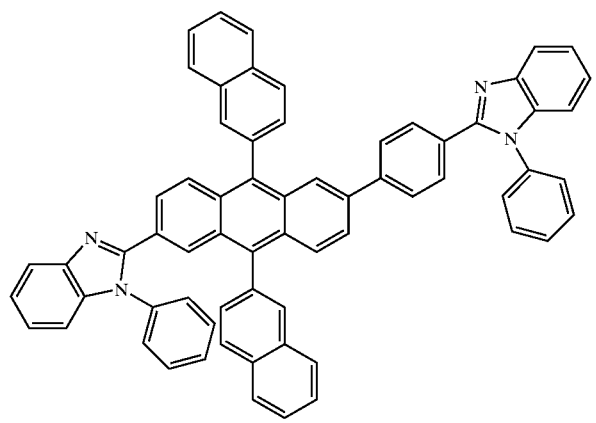

(5-4)

(Chemical Formula 5-5)

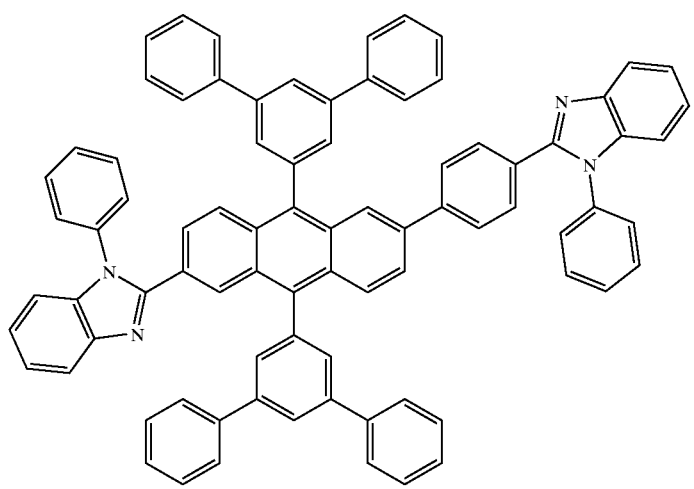

(5-5)

The above compounds are presented in order to aid understanding of the invention, and the compounds provided by the invention are not limited to them. For example, the aromatic moiety of the imidazole group can be substituted with groups such as $C_1$–$C_{20}$ alkyl, alkoxy or aromatic hydrocarbons, substituted or unsubstituted heterocyclic or aromatic groups, or halides such as Cl, Br, F or I. Also, the imidazole group can have more than one substitution on the benzene ring, and this substitution can have an ortho, meta or para substitution. That is, the imidazole group can be substituted as is shown below:

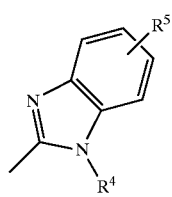

where $R^5$ can be $C_1$–$C_{20}$ alkyl, alkoxy or aromatic hydrocarbons, aryl-substituted silicon groups, aryl-substituted boron groups, substituted or unsubstituted heterocyclic or aromatic groups, or halides such as Cl, Br, F or I.

Also, the anthracene moiety can be further substituted with additional functional groups, as is shown below:

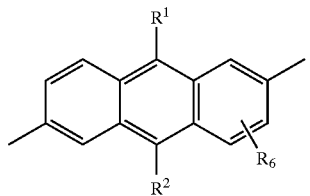

where $R^6$ can be $C_1$–$C_{20}$ alkyl alkoxy or aromatic hydrocarbons, substituted or unsubstituted heterocyclic or aromatic groups, or halides such as Cl, Br, F or I.

Synthesis of the compounds satisfying the above Chemical Formulas 1, 2, 3, 4, and 5 and an organic electroluminescent display using the same will be explained in more detail with reference to the following Examples and Comparative Examples. However, these are to illustrate the invention and the invention is not limited to them, and compounds not described in Examples and satisfying the above Chemical Formulas 1, 2, 3, 4, and 5 are also within the range of the present invention and they can be applied as an organic compound layer of an organic electroluminescent display.

EXAMPLES

In order to synthesize compounds represented by the above Chemical Formulas 1 to 5, a starting material was selected from the compounds of the following Chemical Formulas a to i, and preparations thereof will be described in Preparation Examples 1 to 9.

(Chemical Formula a)

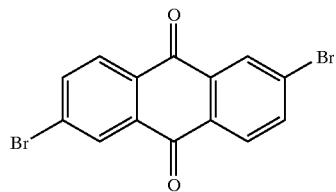

(a)

(Chemical Formula b)

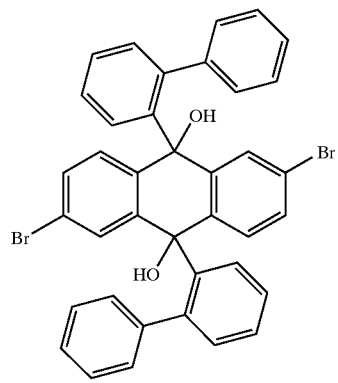

(b)

(Chemical Formula c)

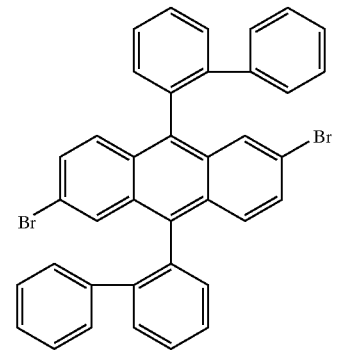

(c)

(Chemical Formula d)

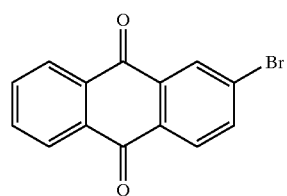

(d)

(Chemical Formula e)

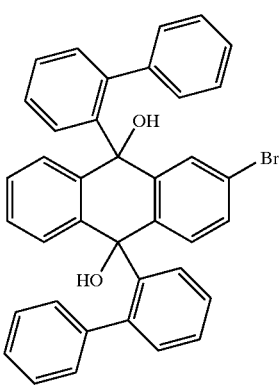

(e)

(Chemical Formula f)

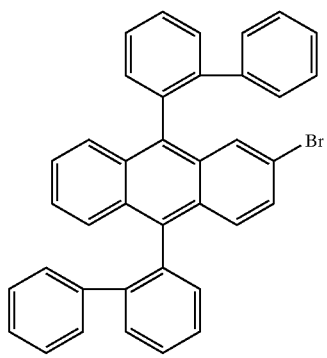
(f)

(Chemical Formula g)

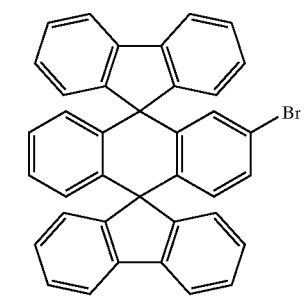
(g)

(Chemical Formula h)

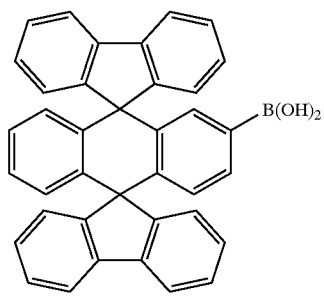
(h)

(Chemical Formula i)

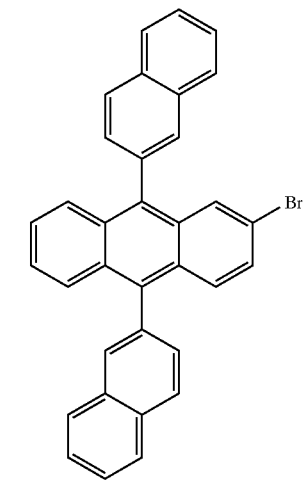
(i)

(Chemical Formula j)

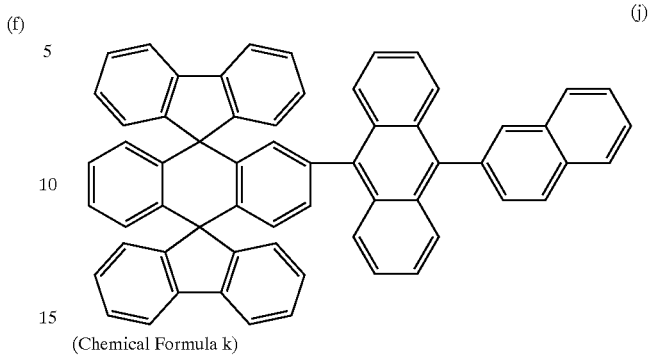
(j)

(Chemical Formula k)

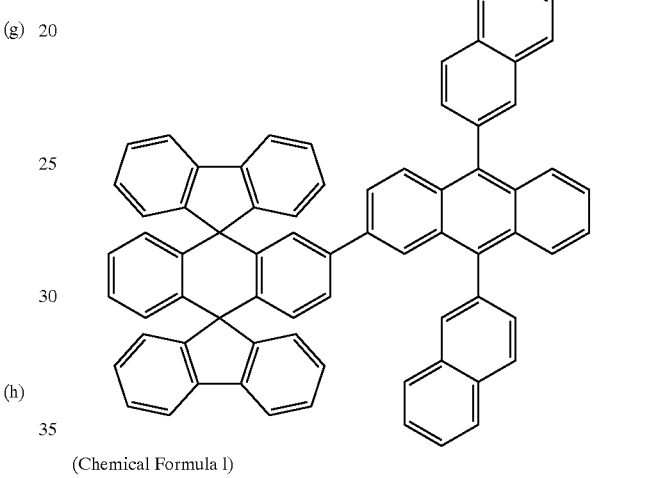
(k)

(Chemical Formula l)

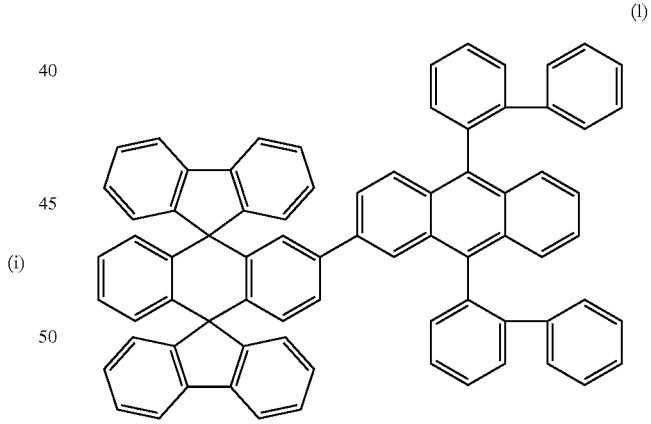
(l)

Preparation Example 1

(Preparation of Starting Material Represented by Chemical Formula a)

2,6-Diaminoanthraquinone (23.8 g, 100 mmol) was dispersed in 48 wt % of a hydrogen bromide aqueous solution, and then sodium nitrite ($NaNO_2$, 14.1 g, 204 mmol) was slowly added at 20° C. After gas evolution was completed, a solution in which copper bromide (CuBr, 29.5 g, 206 mmol) was dissolved in 48 wt % of a hydrogen bromide aqueous solution (63 mL) was slowly added together with a small amount of ethanol (50 mL). The temperature of the reaction mixture was slowly elevated and then the mixture was slowly refluxed. After cooling to room temperature, water was added to dilute the mixture, and the precipitate was filtered off with suction, washed with water, and dried in vacuo. Then it was dissolved in chloroform, filtered through a short column of silica gel, and concentrated under reduced pressure. Purification by column chromatography and recrystallization from chloroform yielded a compound of the Chemical Formula a (10.0 g, 27%).

The analysis result of the compound is as follows.

1H NMR (300 MHz, CDCl$_3$), 8.44 (d, J=2.1 Hz, 2H), 8.18 (d, J=8.0 Hz, 2H), 7.95 (dd, J=2.1, 8.0 Hz, 2H.)

Preparation Example 2

(Preparation of Starting Material Represented by Chemical Formula b)

2-Bromo biphenyl (8.83 mL, 51.2 mmol) was dissolved in dry THF (200 mL) under a nitrogen atmosphere and cooled to −78° C., and then t-butyl lithium (60 mL, 1.7 M pentane solution) was slowly added. After stirring at the same temperature for 40 minutes, the compound of the Chemical Formula a prepared in Preparation Example 1 (7.50 g, 20.5 mmol) was added at the same temperature. The cooling bath was removed, and the mixture was stirred at room temperature for 15 hours. Then it was quenched with diethyl ether (200 mL) and 2 N hydrochloric acid (200 mL) and stirred at room temperature for 40 minutes. The precipitate was filtered off with suction, and washed with water and ethyl ether. The obtained material was dried to obtain a compound of the Chemical Formula b (11.8 g, 85%).

Preparation Example 3

(Preparation of Starting Material Represented by Chemical Formula c)

A mixture of a compound of the Chemical Formula b prepared in Preparation Example 2 (4.00 g, 5.93 mmol), potassium iodide (9.85 g, 59.3 mmol), and sodium hypophosphite hydrate (10.4 g, 98.0 mmol) was refluxed in a mixture of acetic acid (80 mL) and ortho-dichlorobenzene (600 mL). After cooling to room temperature, the reaction mixture was extracted with chloroform, dried over magnesium sulfate, and concentrated under reduced pressure. The obtained solid was dissolved in chloroform, passed through a short silica gel column, and concentrated under reduced pressure. The solid was dispersed in n-hexane, agitated and filtered, and then vacuum dried to obtain a light yellow compound of the Chemical Formula c (3.30 g, 87%).

The analysis result of the compound is as follows:

m.p. 478.1; 1H NMR (300 MHz, CDCl3) 7.92 (d, J=7.6 Hz, 4H), 7.46 (t, J=8.0 Hz, 4H), 7.33 (t, J=7.4 Hz, 4H), 7.21 (d, J=7.6 Hz, 4H), 6.88 (dd, J=2.1, 8.6 Hz, 2H), 6.47 (d, J=2.1 Hz, 2H), 6.22 (d, J=8.6 Hz, 2H); MS (M+) 636; Anal. Calc'd. for $C_{38}H_{22}Br_2$: C, 71.50; H, 3.47; Br, 25.03. Found: C, 71.90; H, 3.40; Br, 25.7.

Preparation Example 4

(Preparation of Starting Material Represented by Chemical Formula d)

Copper bromide ($CuBr_2$, 17.9 g, 80.0 mmol) and t-butyl nitrite (12 mL, 101 mmol) were dispersed in acetonitrile (250 mL) at 65° C., and agitated, and then 2-aminoanthraquinone (15.0 g, 67.2 mmol) was slowly added dropwise over 5 minutes. After gas evolution was completed, the mixture was cooled to room temperature, quenched with 20% hydrochloric acid (1,000 mL), and extracted with dichloromethane. The organic extract was dried over magnesium sulfate and concentrated under reduced pressure. Purification by column chromatography (dichloromethane/n-hexane=4/1) yielded a compound of the Chemical Formula d (14.5 g, 75%).

The analysis result of the compound is as follows:

m.p. 207.5; 1H NMR (500 MHz, CDCl$_3$), 8.43 (d, J=1.8 Hz, 1H), 8.30 (m, 2H), 8.17 (d, J=8.3 Hz, 1H), 7.91 (dd, J=1.8, 8.3 Hz, 1H), 7.82 (m, 2H); MS (M+) 286; Anal. Calc'd. for $C_{14}H_7BrO_2$: C, 58.57; H, 2.46; Br, 27.83; O, 11.14. Found: C, 58.88; H, 2.39; Br, 27.80; O, 10.93.

Preparation Example 5

(Preparation of Starting Material Represented by the Chemical Formula e)

2-Bromo biphenyl (9.0 mL, 52 mmol) was dissolved in dried tetrahydrofuran (100 mL) under a nitrogen atmosphere, and t-butyl lithium (40 mL, 1.7 M pentane solution) was slowly added at −78° C. After stirring at the same temperature for 1 hour, the compound of the Chemical Formula d prepared in Preparation Example 4 (4.9 g, 17 mmol) was added. Aqueous ammonium chloride solution was added to the mixture, and then it was extracted with methylene chloride. The organic extract was dried over magnesium sulfate and concentrated under reduced pressure. The obtained solid was dispersed in ethanol, stirred for 1 hour, filtered off with suction, and washed with ethanol. After drying, a compound of the Chemical Formula e (9.50 g, 94%) was obtained.

Preparation Example 6

(Preparation of Starting Material Represented by Chemical Formula f)

The compound of Chemical Formula e prepared in Preparation Example 5 (6.00 g, 10.1 mmol) was dispersed in 300 mL of acetic acid under a nitrogen atmosphere, and then potassium iodide (16.8 g, 101 mmol) and sodium hypophosphite hydrate (17.7 g, 167 mmol) were added, and the mixture was agitated while boiling for 3 hours. After cooling to room temperature, the mixture was filtered and washed with water and methanol, and then vacuum dried to obtain a light yellow compound of the Chemical Formula f (5.0 g, 88%).

Preparation Example 7

(Preparation of Starting Material Represented by Chemical Formula g)

The compound of the Chemical Formula e prepared in Preparation Example 5 (9.5 g, 16 mmol) was dispersed in 100 mL of acetic acid, and 5 drops of concentrated sulfuric acid were added thereto, and the mixture was refluxed for 3 hours. The mixture was cooled to room temperature, and the precipitate was filtered, washed with acetic acid, and then washed with water and ethanol in this order. After drying, the solid was purified by sublimation to obtain a white solid compound of the Chemical Formula g (8.0 g, 89%).

Preparation Example 8

(Preparation of Starting Material Represented by Chemical Formula h)

The compound of Chemical Formula g prepared in Preparation Example 7 (10.0 g, 17.9 mmol) was completely dissolved in 150 mL of dry THF under a nitrogen atmosphere, and then t-butyl lithium (31.5 mL, 1.7 M pentane solution) was slowly added at −78° C. After stirring at the same temperature for 1 hour, trimethylborate (8 mL, 71.5 mmol) was added. The cooling bath was removed and the reaction mixture was stirred at room temperature for 3 hours. Then, it was quenched with 2 N hydrochloric acid solution (100 mL) and stirred at room temperature for 1.5 hours. The precipitate was filtered, washed with water and ethyl ether in this order, and dried in vacuo. After drying, the crude product was dispersed in ethyl ether, stirred for 2 hours, filtered, and dried to obtain a white compound of the Chemical Formula h (7.6 g, 81%).

Preparation Example 9

(Preparation of Starting Material Represented by Chemical Formula i)

2-Bromonaphthalene (11.0 g, 53.1 mmol) was dissolved in dry tetrahydrofuran (100 mL) under a nitrogen atmosphere, and t-butyllithium (47.0 mL, 1.7 pentane solution) was slowly added at −78° C. After agitating at the same temperature for 1 hour, the compound of the Chemical Formula d prepared in Preparation Example 4 (6.31 g, 22.0 mmol) was added. The cooling bath was removed and the reaction mixture was stirred at room temperature for 3 hours. After adding an aqueous ammonium chloride solution to the reaction mixture, the reaction mixture was extracted with methylene chloride. The organic extract was dried over magnesium sulfate and concentrated under reduced pressure. The crude product was dissolved in diethyl ether, and then petroleum ether was added and the mixture was agitated for several hours to obtain a solid compound. The solid was filtered and vacuum dried to obtain dinaphthyl dialcohol (11.2 g, 94%). Dinaphthyl dialcohol, synthesized above, (11.2 g, 20.6 mmol) was dispersed in 600 mL of acetic acid under a nitrogen atmosphere, and then potassium iodide (34.2 g, 206 mmol) and sodium hypophosphite hydrate (36.0 g, 340 mmol) were added, and the mixture was agitated while boiling for 3 hours. After cooling to room temperature, the mixture was filtered and washed with water and methanol, and then vacuum dried to obtain a light yellow compound of the Chemical Formula i (10.1 g, 96%).

Example 1

(Preparation of a Compound Represented by the Chemical Formula 2-2)

4-Bromophenylaldehyde (41.6 g, 225 mmol) and 1,3-propandiol (16.3 mL, 225 mmol) were dissolved in 500 mL of toluene, and then 1 g of p-toluene sulfonic acid was added and the mixture was refluxed for 2 days while removing water. 100 mL of diethyl ether was added to the mixture to dilute it, and it was quenched with 100 mL of water. The organic extract was dried over magnesium sulfate and concentrated under reduced pressure. Purification by column chromatography and crystallization from petroleum ether yielded 4-bromophenylacetal (45.0 g, 82%) as a white solid.

To a solution of 4-bromophenylacetal (5.00 g, 20.6 mmol) in dry THF (100 mL) was added dropwise t-butyl lithium (24.2 mL, 1.7 M pentane solution) at −78° C. After the mixture was agitated for 1 hour, trimethylborate (7 mL, 62.4 mmol) was slowly added at −78° C., then the reaction temperature was slowly elevated and the mixture was agitated at room temperature for 3 hours.

The reaction mixture was poured into 200 mL of a 2 N hydrochloric acid, stirred for 1 hour, filtered, washed with water and ether, and dried to obtain white 4-formylphenylboronic acid (2.50 g, 81%).

The compound of Chemical Formula c prepared in Preparation Example 3 (0.40 g, 0.62 mmol) and 4-formylphenylboronic acid (1.10 g, 7.34 mmol) were added to a solution of 10 mL of 2 N potassium carbonate solution and 30 mL of toluene, and $Pd(PPh_3)_4$ (0.16 g, 0.14 mmol) was added while stirring, and the mixture was refluxed for 3 days. The organic layer was separated, washed with water, dried over magnesium sulfate, passed through a silica gel column, and concentrated under reduced pressure. The crude product was dispersed in 40 mL of ethanol, filtered, and recrystallized from chloroform to obtain dialdehyde (155 mg, 36%).

Dialdehyde (120 mg, 0.17 mmol) and N-phenyl-1,2-phenylenediamine (83 mg, 0.45 mmol) were introduced into a solution of 20 ml of toluene and 10 ml of acetic acid. The mixture was refluxed for 2 days, cooled to room temperature, filtered off with suction, and washed with ethanol. The obtained solid was washed with 100 ml of chloroform and dried to obtain a pure compound represented by Chemical Formula 2-2 (120 mg, 68%).

The analysis result of the compound is as follows:

m.p. 395.0; 1H NMR (300 MHz, $CDCl_3$) 7.88(2H), 7.62(2H), 7.66–7.60(10H), 7.55–7.44(15H), 7.40(2H), 7.38–30(9H), 6.95(6H), 6.83(4H); MS [M+H] 1019.

Example 2

(Preparation of a Compound Represented by Chemical Formula 1-2)

The compound represented by the Chemical Formula f prepared in Preparation Example 6 (1.00 g, 1.80 mmol) and 4-formylphenylboronic acid (0.74 g, 4.93 mmol) were introduced into a solution of 20 mL of 2 N potassium carbonate solution and 40 mL of toluene, $Pd(PPh_3)_4$ (0.20 g, 0.17 mmol) was added while stirring, and the mixture was refluxed for 3 days. The organic layer was separated, washed with water, dried over magnesium sulfate, passed through a silica gel layer, and concentrated under reduced pressure to obtain a solid compound. The solid was dispersed in 100 mL of ethanol, filtered, and recrystallized from ethyl acetate to obtain anthracene phenylaldehyde (330 mg, 31%).

A mixture of anthracene phenylaldehyde (0.33 g, 0.56 mmol) and N-phenyl-1,2-phenylenediamine (0.11 g, 0.60 mmol) in a mixture of 40 mL of toluene and 10 mL of acetic acid was refluxed for 2 days. After cooling to room temperature, the precipitate was filtered, washed with ethanol and chloroform, and dried to obtain a compound of Chemical Formula 1-2 (120 mg, 28%).

The analysis result of the compound is as follows:

1H NMR (300 MHz, $CDCl_3$) 7.89(1H), 7.75(1H), 7.62–7.29 (24H), 6.98–6.76(12H); MS [M+H] 751.

Example 3

(Preparation of a Compound Represented by Chemical Formula 1-4)

The compound of Chemical Formula i prepared in Preparation Example 9 (4.00 g, 7.85 mmol) and 4-formylphenylboronic acid (3.53 g, 23.5 mmol) were introduced into a solution of 20 mL of 2 N potassium carbonate solution and 60 mL of toluene, $Pd(PPh_3)_4$ (0.27 g, 0.23 mmol) was added while stirring, and the mixture was refluxed for 3 days. The organic layer was separated, washed with water, dried over magnesium sulfate, and passed through a silica gel layer, and concentrated to obtain a solid compound. The solid was dispersed in 100 mL of ethanol, filtered, and recrystallized from ethyl acetate to obtain anthracene phenylaldehyde (2.00 g, 47.6%).

A mixture of anthracene phenylaldehyde (2.00 g, 3.74 mmol) and N-phenyl-1,2-phenylenediamine (0.69 g, 3.74 mmol) in a mixture of 40 mL of toluene and 10 mL of acetic acid was refluxed for 2 days. After cooling to room temperature, the formed solid was filtered, washed with ethanol and chloroform, and dried to obtain a solid of Chemical Formula 1-4 (1.30 g, 49.7%).

The analysis result of the compound is as follows:

m.p. 352.0; 1H NMR (300 MHz, $CDCl_3$) 8.28(s, 2H), 8.14(d, 2H), 7.99(t, 4H), 7.81(t, 4H), 7.62(m, 4H), 7.53(d, 2H), 7.45(m, 4H), 7.32–7.26(m, 6H); MS [M+H] 699.

Example 4

(Preparation of a Compound Represented by Chemical Formula 2-4)

To a solution of 2-bromo naphthalene (5.78 g, 28.0 mmol) in dry THF (40 mL) under a nitrogen atmosphere was added dropwise cooled t-butyl lithium (21 mL, 1.7 M pentane solution) at −78° C. After stirring at the same temperature for 40 minutes, the compound of the Chemical Formula a prepared in Preparation Example 1 (2.93 g, 8.00 mmol) was added at the same temperature. After removing the cooling bath, the mixture was stirred at room temperature for 3 hours. An ammonium chloride solution (40 mL) was slowly added to the reaction mixture and the mixture was stirred at room temperature for 40 minutes. The precipitate was filtered off with suction, washed with water and petroleum, and dried to obtain the dialcohol (4.10 g, 82%).

A mixture of the dialcohol (4.10 g, 6.59 mmol), potassium iodide (10.9 g, 65.9 mmol), and sodium hypophosphite hydrate (11.6 g, 109 mmol) was refluxed in acetic acid (200 mL) for 24 hours. The mixture was cooled to room temperature, filtered, washed with water and petroleum ether in this order, and dried to obtain 2,6-dibromo-9,10-dinaphthalene-2-yl-anthracene (3.15 g, 81%).

2,6-Dibromo-9,10-dinaphthalene-2-yl-anthracene (3.15 g, 5.35 mmol) and 4-formylphenylboronic acid (2.81 g, 18.7 mmol) were introduced into a solution of 20 mL of 2 N potassium carbonate solution and 100 mL of toluene, $Pd(PPh_3)_4$ (0.25 g, 0.22 mmol) was introduced while agitating, and the mixture was refluxed for 15 hours. The organic layer was separated, washed with water, dried over magnesium sulfate. Purification by column chromatography yielded dinaphthyl anthracene phenyldialdehyde (2.77 g, 81%).

A mixture of dinaphthyl anthracene phenyldialdehyde (2.77 g, 4.34 mmbl) and N-phenyl-1,2-phenylenediamine (2.00 g, 10.9 mmol) in a mixture of 120 mL of toluene and 60 mL of acetic acid was refluxed for 15 hours, manganese oxide (1.51 g, 17.4 mmol) was introduced, and the mixture was further reacted for 2 hours. After cooling to room temperature, the formed solid was filtered, washed with ethanol and chloroform, and dried again to obtain a compound of Chemical Formula 2-4 (1.52 g, 36%).

Example 5

(Preparation of a Compound Represented by Chemical Formula 3-2)

9,10-Dioxo-9,10-dihydro-anthracene-2-carbaldehyde (1.63 g, 6.9 mmol) and N-phenyl-1,2-phenylenediamine (1.27 g, 6.90 mmol) were introduced into a mixture of 80 mL of toluene and 10 mL of acetic acid, and the mixture was refluxed for 12 hours. Solvent was removed and ethanol was poured therein to crystallize it, and then the precipitate was filtered to obtain a benzoimidazole compound ([2-(1-phenyl-1H-benzoimidazole-2-yl)-anthraquinone], 1.14 g, 41%).

To a solution of 2-bromobiphenyl (1.1 mL, 6.25 mmol) in dry tetrahydrofuran (50 mL) was added dropwise t-butyl lithium (8.3 mL, 1.5 M pentane solution) at −78° C. After stirring for 30 minutes at the same temperature, 2-(1-phenyl-1H-benzoimidazole-2-yl)-anthraquinone (1.00 g, 2.50 mmol), synthesized above, was slowly added to the mixture, and then the mixture was agitated at room temperature for 4 hours. It was then poured into a mixture of 2 N hydrochloric acid and ethyl ether and stirred for 1 hour. The precipitate was filtered and dried to obtain 9,10-bis[biphenyl-2-yl-(1-phenyl-1H-benzoimidazole-2-yl)]-9,10-dihydro-anthracene-9,10-dialcohol (1.00 g, 57%).

The dialcohol (0.70 g, 1.00 mmol) was dispersed in 60 mL of acetic acid under a nitrogen atmosphere, and potassium iodide (1.66 g, 10 mmol) and sodium hypophosphite hydrate (1.66 g, 15.7 mmol) were added, and then the mixture was agitated while boiling. The mixture was cooled to room temperature, filtered, washed with water and methanol, and dried to obtain a light yellow compound of Chemical Formula 3-2 (0.45 g, 67%).

The analysis result of the compound is as follows:

m.p. 270.0; 1H NMR (300 MHz, $CDCl_3$) 7.86(d, 1H), 7.75(dd, 1H), 7.70(s, 1H), 7.63–7.48(m, 8H), 7.42–7.0(m, 12H), 6.92–6.81(m, 9H), 6.63(d, 2H); MS [M+H] 675.

Example 6

(Manufacture of an Organic Electroluminescent Device)

A glass substrate on which ITO (indium tin oxide) was coated in a thin film at a thickness of 1,500 Å was introduced into distilled water in which detergent was dissolved, and it was washed using ultrasonic waves. As the detergent, a Fischer Co. product was used, and the distilled water was filtered twice with a filter from Millipore Co. The ITO was washed for 30 minutes, and ultrasonic cleaning was conducted twice in sequence with distilled water for 10 minutes each time. After washing with distilled water, ultrasonic cleaning was conducted with a solvent such as isopropyl alcohol, acetone, methanol, etc., and the substrate was dried and transferred to a plasma cleaning apparatus. The substrate was then cleaned using oxygen plasma for 5 minutes, and transferred to a vacuum deposition apparatus.

On the prepared ITO transparent electrode, hexanitrile hexaazatriphenylene was thermal-vacuum deposited with a thickness of 500 Å to form a hole injection layer. NPB, which transports holes, was vacuum deposited thereon (600 Å), and Alq3 that performs a function of the emitting layer was vacuum deposited with a thickness of 300 Å. On the emitting layer, a compound of the Chemical Formula 1-4, that performs functions of injecting and transporting electrons, was vacuum deposited with a thickness of 200 Å to form a thin film of an organic material layer. On the electron injection and transportation layer, lithium fluoride (LiF) with a thickness of 5 Å and aluminum with a thickness of 2500 Å were sequentially deposited to form a cathode using shadow mask to fabricate 6 $mm^2$ of test pixel. The deposition rate of the organic material was maintained at 1 Å/sec, that of lithium fluoride was 0.2 Å/sec, and that of aluminum was 3–7 Å/sec.

On the prepared organic electroluminescent device, a forward electric field of 5.4 V was added, and as result, a green spectrum with a brightness of 1,656 nit, corresponding to x=0.34, y=0.55 on the basis of 1,931 CIE color coordinate, was observed at a current density of 50 mA/$cm^2$.

Figure 2:
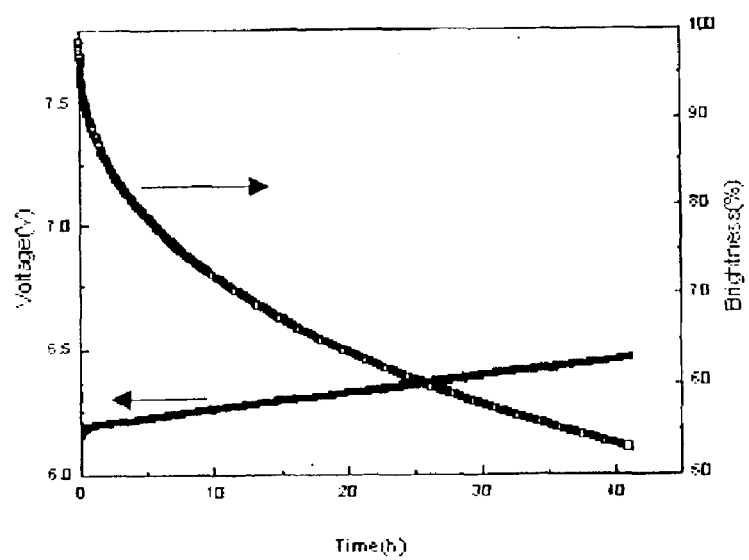
FIG. 2 shows the brightness of the device of Example 6 as a function of driving time.
Figure 5:
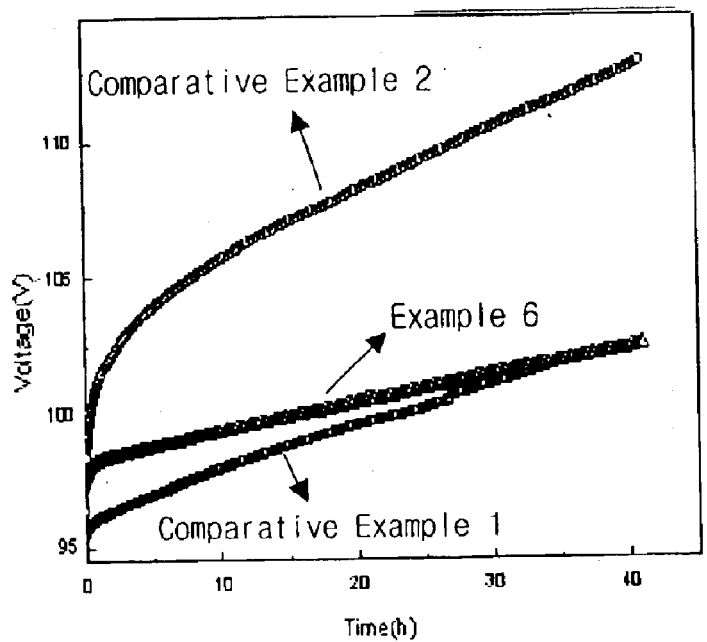
FIG. 5 shows the voltages of Example 6, Comparative Example 1 and Comparative Example 2 as a function of driving time.

The half-lifetime of the device was measured by applying 200 mA/$cm^2$ of constant DC current density. The changes of brightness and driving voltage were monitored to evaluate the performance of the claiming compounds relative to the existing compounds. As shown in FIG. 2, after 40 hours of driving, the brightness of the device drops to a 53% level and the driving voltage was increased to 6.4 V, which corresponds to 102% of the initial driving voltage (See FIG. 5).

Comparative Example 1

(Manufacture of Organic Electroluminescent Device)

On the ITO transparent electrode prepared in Example 6, hexanitrile hexaazatriphenylene was thermal-vacuum deposited with a thickness of 500 Å to form a hole injection layer. NPB, which transports holes, was vacuum deposited thereon (600 Å), and Alq3 that performs functions of both emitting layer and electron transporting layer was vacuum deposited with a thickness of 500 Å. On the Alq3 layer, lithium fluoride (LiF) with a thickness of 5 Å and aluminum with a thickness of 2,500 Å were sequentially deposited to form a cathode using shadow mask to fabricate 6 mm² of test pixel. The deposition rate of the organic material was maintained at 1 Å/sec, that of lithium fluoride was 0.2 Å/sec, and that of aluminum was 3–7 Å/sec.

On the prepared organic electroluminescent device, a forward electric field of 6.4 V was added, and as result, a green spectrum with a brightness of 1,774 nit, corresponding to x=0.34, y=0.56 on the basis of 1,931 CIE color coordinate, was observed at a current density of 50 mA/cm². This result shows that the introduction of the electron transporting layer of this invention lowers the driving voltage as shown in Example 6.

Figure 3:
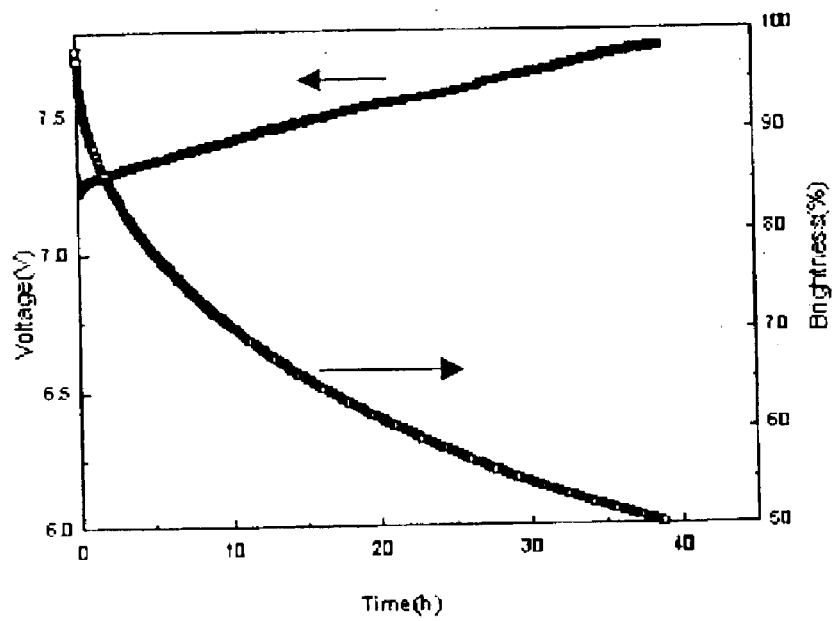
FIG. 3 shows the brightness of the device of Comparative Example 1 as a function of driving time.

The half-lifetime of the device was measured by applying 200 mA/cm² of constant DC current density. As shown in FIG. 3, after 38 hours of driving, the brightness of the device drops to 50% level and the driving voltage was increased to 7.7 V, which corresponds to 102% of the initial driving voltage (See FIG. 5).

Comparative Example 2

(Manufacture of Organic Electroluminescent Device)

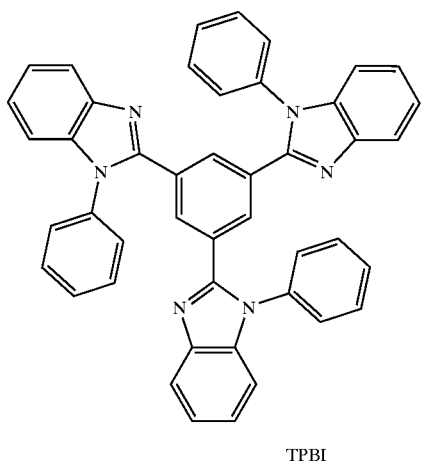

TPBI

On the ITO transparent electrode prepared in Example 6, hexanitrile hexaazatriphenylene was thermal-vacuum deposited with a thickness of 500 Å to form a hole injection layer. NPB, which transports holes, was vacuum deposited thereon (600 Å), and Alq3 that performs a function of the emitting layer was vacuum deposited with a thickness of 300 Å. On the emitting layer, TPBI that performs functions of injecting and transporting electrons was vacuum deposited with a thickness of 200 Å to form a thin film of an organic material layer. On the electron transporting layer, lithium fluoride (LiF) with a thickness of 5 Å and aluminum with a thickness of 2,500 Å were sequentially deposited to form a cathode using shadow mask to fabricate 6 mm² of test pixel. The deposition rate of the organic material was maintained at 1 Å/sec, that of lithium fluoride was 0.2 Å/sec, and that of aluminum was 3–7 Å/sec.

Figure 4:
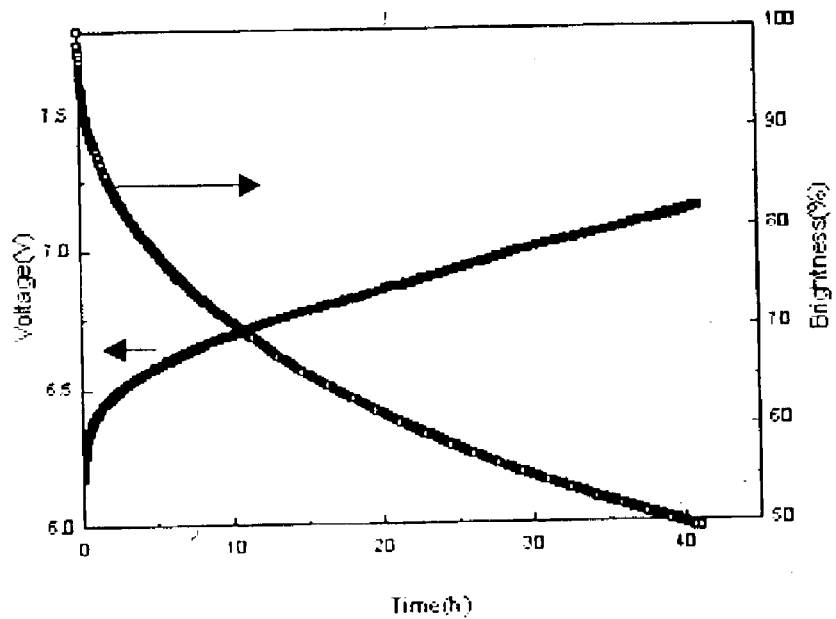
FIG. 4 shows the brightness of the device of Comparative Example 1 as a function of driving time.

On the prepared organic electroluminescent device, a forward electric field of 5.5 V was added, and as result, a green spectrum with a brightness of 1,655 nit, corresponding to x=0.34, y=0.56 on the basis of 1,931 CIE color coordinate, was observed at a current density of 50 mA/cm The half-lifetime of the device was measured by applying 200 mA/cm² of constant DC current density. As shown in FIG. 4, after 40 hours of driving, the brightness of the device drops to 50% level and the driving voltage was increased to 7.2 V, which corresponds to 113% of the initial driving voltage (See FIG. 5). This comparative result shows that the electron transporting material of the invention provides an organic electroluminescent device which can minimize driving voltage increase during operation.

Example 7

(Manufacture of Organic Electroluminescent Device)

The following experiment was performed to test the stability of the inventive compound to hole carriers by using it as an emitting material in which holes and electrons recombine to emit light. When a p-type emitting material (hole mobility>electron mobility) or a proper amount of p-type dopant is used in an emitting layer, hole carriers can be transferred into the electron transport layer. Therefore if the material composing the electron transporting layer is unstable to holes, the device can be easily destroyed, not because of the instability of the emitting material but because of the electron transporting material.

On the ITO transparent electrode prepared in Example 6, hexanitrile hexaazatriphenylene was thermal-vacuum deposited with a thickness of 500 Å to form a hole injection layer. NPB, which transports holes, was vacuum deposited thereon (600 Å), and a compound of Chemical Formula 1-4 that performs a function of the emitting layer was vacuum deposited with a thickness of 400 Å. On the emitting layer, Alq3 that performs functions of injecting and transporting electrons was vacuum deposited with a thickness of 200 Å to form a thin film of an organic material layer. On the electron transporting layer, lithium fluoride (LiF) with a thickness of 5 Å and aluminum with a thickness of 2,500 Å were sequentially deposited to form a cathode using shadow mask to fabricate 6 mm² of test pixel. The deposition rate of the organic material was maintained at 1 Å/sec, that of lithium fluoride was 0.2 Å/sec, and that of aluminum was 3–7 Å/sec.

On the prepared organic electroluminescent device, a forward electric field of 6.6 V was added, and as result, a blue light emission with a brightness of 733 nit (peak max. located at 460 nm), was observed at a current density of 50 mA/cm².

Figure 6:
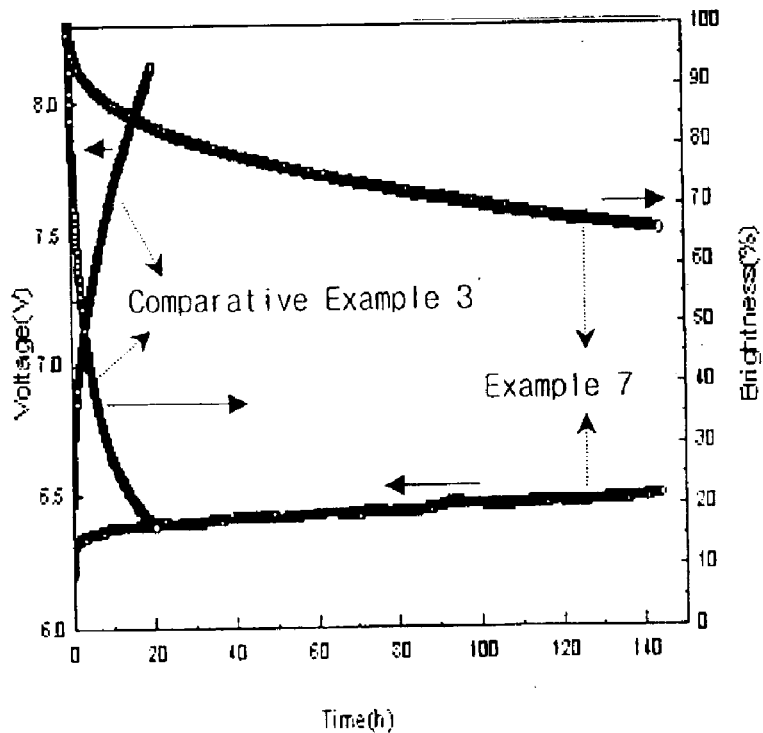
FIG. 6 shows the brightness of the device of Example 7 as a function of driving time.
Figure 7:
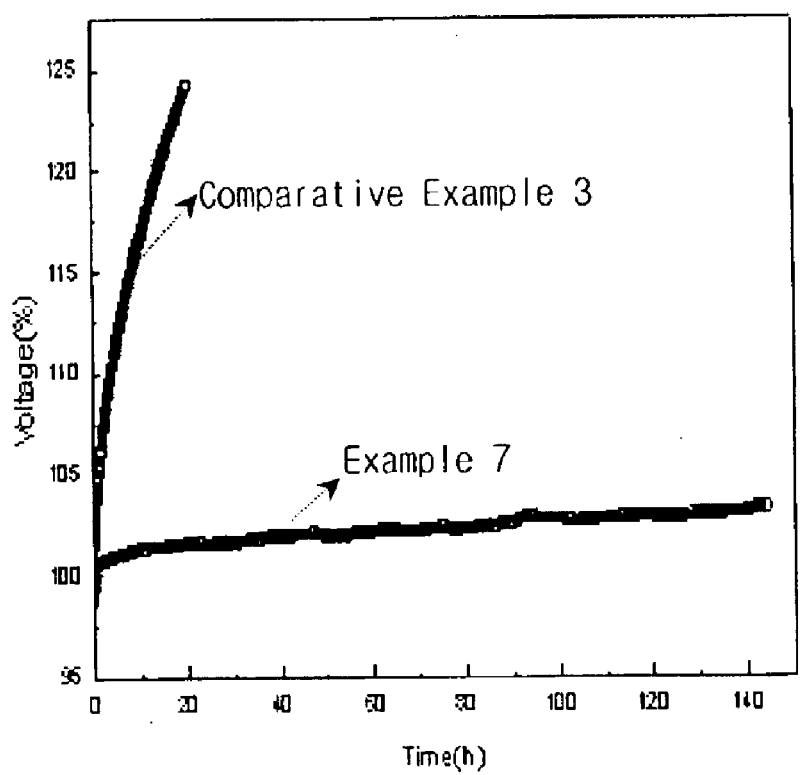
FIG. 7 shows the voltages of Example 7 and Comparative Example 3 as a function of driving time.

The half-lifetime of the device was measured by applying 50 mA/cm² of constant DC current density. As shown in FIG. 6, after 140 hours of driving, the brightness of the device drops to a 67% level and the driving voltage was increased to 6.5 V, which corresponds to 103% of the initial driving voltage (See FIG. 7). This result shows that the material claiming in this patent application is stable to hole carriers and also can be used as an blue emitting source with enhanced device lifetime.

Comparative Example 3

(Manufacture of Organic Electroluminescent Device)

An electroluminescent device was prepared in the same manner as Example 6, except the TPBI is used as an emitting material instead of a compound of the Chemical Formula 1-4.

On the prepared organic electroluminescent device, a forward electric field of 6.9 V was added, and as result, a blue light emission with a brightness of 354 nit (peak max. located at 440 nm), was observed at a current density of 50 mA/cm$^2$.

The half-lifetime of the device was measured by applying 50 mA/cm$^2$ of constant DC current density. As shown in FIG. 6, after 20 hours of driving, the brightness of the device drops to a 20% level of the initial brightness and the driving voltage was increased to 8.2 V, which corresponds to 124% of the initial driving voltage (See FIG. 7). This comparative result shows that the material of the invention is stable to hole carriers and also can be used as a blue emitting source with enhanced device lifetime.

Example 8

(Manufacture of Organic Electroluminescent Device)

On the ITO transparent electrode prepared in Example 6, hexanitrile hexaazatriphenylene was thermal-vacuum deposited with a thickness of 500 Å to form a hole injection layer. NPB, which transports holes, was vacuum deposited thereon (600 Å), and a compound represented by the Chemical Formula j that performs a function of the emitting layer was vacuum deposited with a thickness of 100 Å. On the emitting layer, a compound of the Chemical Formula 1-2 that performs functions of injecting and transporting electrons was vacuum deposited with a thickness of 200 Å to form a thin film of an organic material layer. On the electron injection and transportation layer, lithium fluoride (LiF) with a thickness of 5 Å and aluminum with a thickness of 2,500 Å were sequentially deposited to form a cathode using shadow mask to fabricate 6 mm$^2$ of test pixel. The deposition rate of the organic material was maintained at 1 Å/sec, that of lithium fluoride was 0.2 Å/sec, and that of aluminum was 3–7 Å/sec.

On the prepared organic electroluminescent device, a forward electric field of 4.04 V was added, and as result, a blue spectrum with a brightness of 184 nit, corresponding to x=0.16, y=0.11 on the basis of 1,931 CIE color coordinate, was observed at a current density of 10 mA/cm$^2$.

Example 9

(Manufacture of Organic Electroluminescent Device)

On the ITO transparent electrode prepared in Example 6, hexanitrile hexaazatriphenylene was vacuum deposited with a thickness of 500 to form a hole injection layer. NPB (600 Å), which transports holes, was vacuum deposited thereon, and then a compound represented by the Chemical Formula l that performs a function of a emitting layer was vacuum deposited with a thickness of 200 Å. On the emitting layer, a compound represented by the Chemical Formula 2-2 that performs functions of electron injection and transportation was vacuum deposited with a thickness of 200 Å to form a thin film of an organic material layer. On the electron injection and transportation layer, lithium fluoride (LiF) with a thickness of 5 Å and aluminum with a thickness of 2,500 Å were sequentially deposited to form a cathode using shadow mask to fabricate 6 mm$^2$ of test pixel. The deposition rate of the organic material was maintained at 1 Å/sec, that of lithium fluoride was 0.2 Å/sec, and that of aluminum was 3–7 Å/sec.

On the manufactured organic electroluminescent device, a forward electric field of 4.63 V was added, and as result, a blue spectrum with a brightness of 226 nit, corresponding to x=0.16, y=0.19 on the basis of 1,931 CIE coordinate, was observed at a current density of 10 mA/cm$^2$.

Example 10

(Manufacture of an Organic Electroluminescent Device)

On the ITO transparent electrode prepared in Example 6, hexanitrile hexaazatriphenylene was thermal vacuum deposited with a thickness of 500 Å to form a hole injection layer. NPB, which transports holes, was vacuum deposited thereon (600 Å), and a compound represented by the Chemical Formula k functioning as a emitting layer was vacuum deposited with a thickness of 200 Å. On the emitting layer, a compound represented by the Chemical Formula 3-2 that performs functions of electron injection and transportation was vacuum deposited with a thickness of 200 Å to form a thin film of an organic material layer. On the electron injection and transportation layer, lithium fluoride (LiF) with a thickness of 5 Å and aluminum with a thickness of 2,500 Å were sequentially vacuum deposited to form a cathode using shadow mask to fabricate 6 mm$^2$ of test pixel. The deposition rate of the organic material was maintained at 1 Å/sec, that of lithium fluoride was 0.2 Å/sec, and that of aluminum was 3–7 Å/sec.

On the manufactured organic electroluminescent device, a forward electric field of 5.17 V was added, and as a result, a blue spectrum with a brightness of 124 nit, corresponding to x=0.16, y=0.12, on the basis of 1,931 CIE color coordinate, was observed at a current density of 10 mA/cm$^2$.

The novel material of the present invention can be contained in an organic compound layer of an organic electroluminescent display to realize improvement in luminescence, efficiency, and life cycle, as well as low-voltage operation.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

What is claimed is:

1. A compound represented by chemical formula 1:

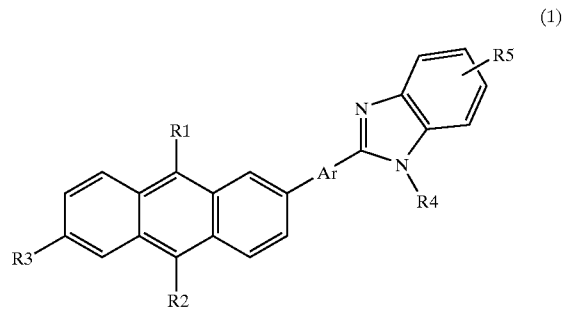

wherein $R^1$ and $R^2$ are a group derived from an aromatic ring;

Ar is a group derived from an aromatic ring;

$R^3$ is a hydrogen atom, a $C_{1-20}$ alkyl group or an aliphatic hydrocarbon, or an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl or alkoxy aryl-substituted silicon groups, aryl-substituted boron groups, substituted or unsubstituted heterocyclic or aromatic groups, Cl, Br, F or I.

2. A compound represented by chemical formula 2:

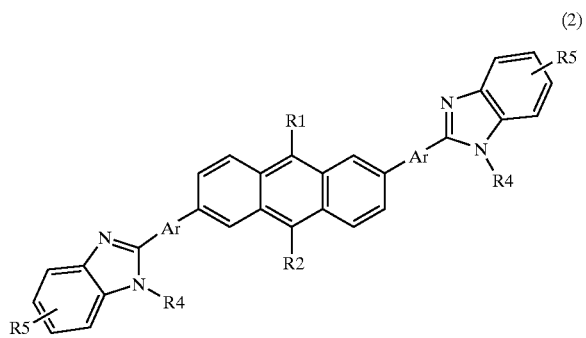

(2)

wherein $R^1$ and $R^2$ are a group derived from an aromatic ring;

Ar is a group derived from an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl, or alkoxy aryl-substituted silicon groups, aryl-substituted boron groups, substituted or unsubstituted heterocyclic or aromatic groups, Cl, Br, F or I.

3. A compound represented by chemical formula 3:

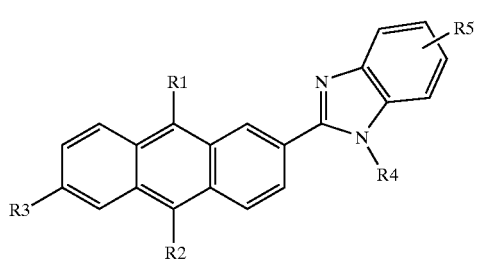

(3)

wherein $R^1$ and $R^2$ are a group derived from an aromatic ring;

$R^3$ is a hydrogen atom, a $C_{1-20}$ alkyl group or an aliphatic hydrocarbon, or an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl or alkoxy aryl-substituted silicon groups, aryl-substituted boron groups, substituted or unsubstituted heterocyclic or aromatic groups, Cl, Br, F or I.

4. A compound represented by chemical formula 4:

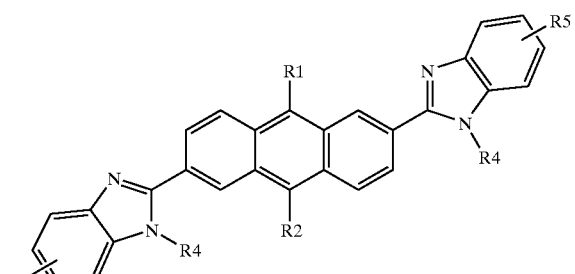

(4)

wherein $R^1$ and $R^2$ are a group derived from an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl or alkoxy aryl-substituted silicon groups, aryl-substituted boron groups, substituted or unsubstituted heterocyclic or aromatic groups, Cl, Br, F or I.

5. A compound represented by chemical formula 5:

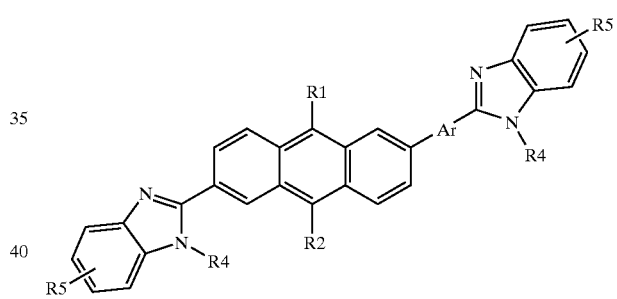

(5)

wherein $R^1$ and $R^2$ are a group derived from an aromatic ring;

Ar is a group derived from an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl or alkoxy aryl-substituted silicon groups, aryl-substituted boron groups, substituted or unsubstituted heterocyclic or aromatic groups, Cl, Br, F or I.

6. An organic electroluminescent display, which comprises:

a pair of electrodes; and at least one organic layer containing at least one compound selected from the group consisting of a compound represented by chemical formula 1, a compound represented by chemical formula 2, a compound represented by chemical formula 3, a compound represented by chemical formula 4, and a compound represented by chemical formula 5:

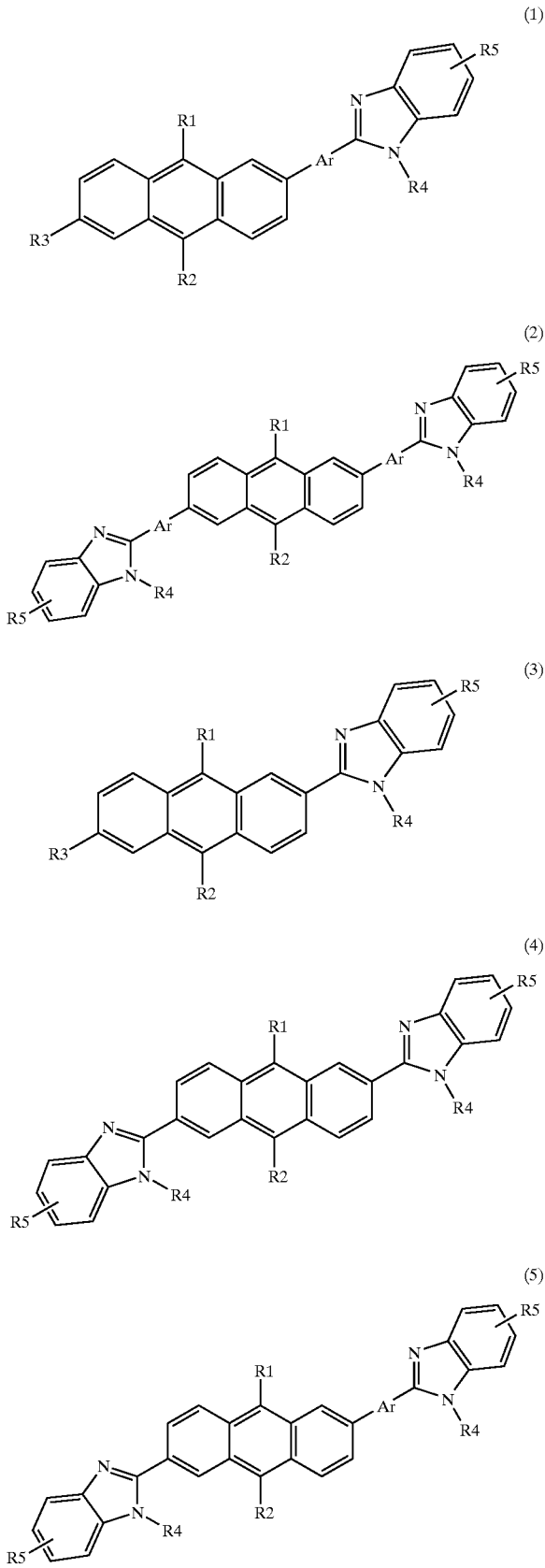

wherein in the above chemical formulas 1, 2, 3, 4, and 5, $R^1$ and $R^2$ are a group derived from an aromatic ring;

Ar is a group derived from an aromatic ring;

$R^3$ is a hydrogen atom, a $C_{1-20}$ alkyl group or an aliphatic hydrocarbon, or an aromatic ring;

$R^4$ is a hydrogen atom, a $C_{1-12}$ alkyl or aliphatic hydrocarbon, or a group derived from an aromatic ring; and $R^5$ is a hydrogen atom, $C_1$–$C_{20}$ alkyl or alkoxy aryl-substituted silicon groups, aryl-substituted boron groups, substituted or unsubstituted heterocyclic or aromatic groups, Cl, Br, F or I.

7. The organic electroluminescent display according to claim 6, wherein at least one of the organic layers is located between an anode that injects holes and a cathode that injects electrons.

8. The organic electroluminescent display according to claim 6, wherein at least one of the organic layers is an electron injection/transporting layer performing functions of electron injection and transportation.

9. The organic electroluminescent display according to claim 6, wherein at least one of the organic layers is an electron injection/transporting and emitting layer performing functions of electron injection and luminescence.

10. The organic electroluminescent display according to claim 6, wherein at least one of the organic layers is an emitting layer performing a function of light emission.

11. The organic electroluminescent display according to claim 6, wherein at least one of the organic layers is an electron transporting and emitting layer performing functions of electron transportation and light emission.

12. The organic electroluminescent display according to claim 6, wherein the organic electroluminescent display comprises a substrate, an anode over the substrate, a hole injection layer over the anode, a hole transportation layer over the hole injection layer, an emitting layer over the transportation layer, an electron transporting layer over the emitting layer and a cathode over the electron transporting layer; and the organic compound is contained in at least the emitting layer.

13. The organic electroluminescent display according to claim 6, wherein the organic electroluminescent display comprises a substrate, an anode over the substrate, a hole injection layer over the anode, a hole transportation layer over the hole injection layer, an emitting layer over the hole transportation layer, an electron injection/transporting layer over the emitting layer, and a cathode over the electron injection/transporting layer; and the organic compound is contained in at least one of the electron injection/transporting layer.

14. The organic electroluminescent display according to claim 6, wherein the organic compound layer comprises a compound of chemical formula 1 or chemical formula 3.

15. The organic electroluminescent display according to claim 6, wherein said display contains at least one compound represented by the chemical formula 1, which is at least one selected from the group consisting of compounds of chemical formulas 1-1, 1-2, 1-3, 1-4, 1-5, 1-6, 1-7, 1-8, 1-9 and 1-10:

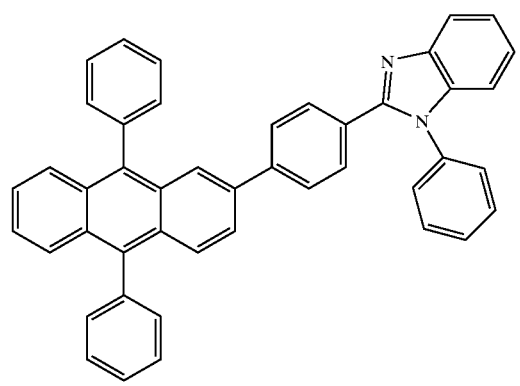 (1-1)
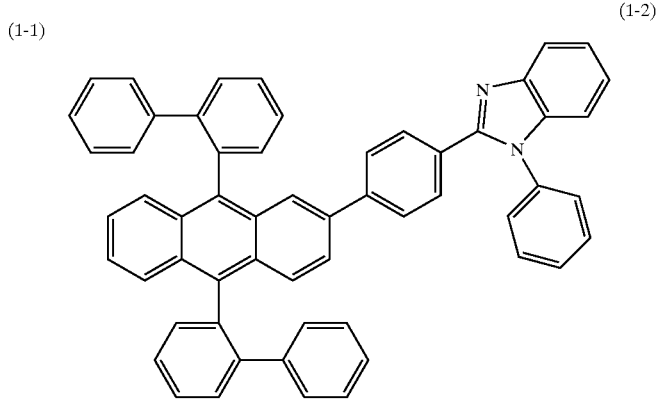 (1-2)
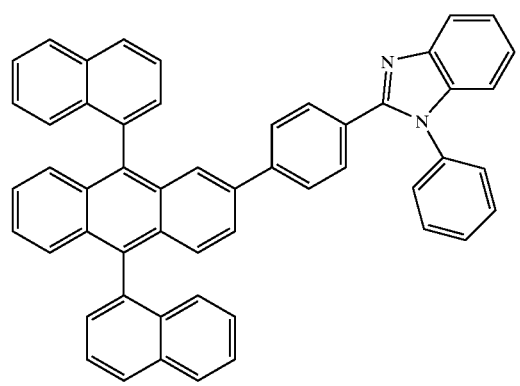 (1-3)
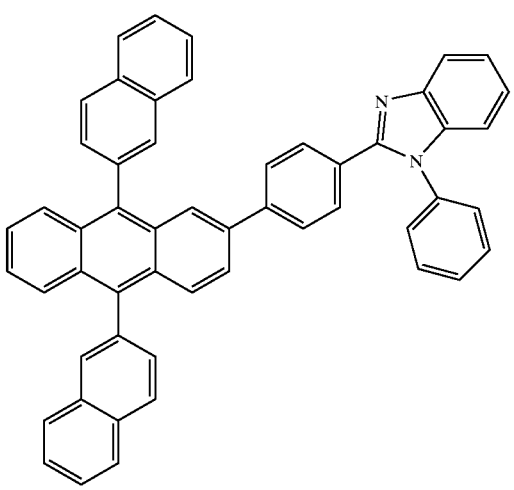 (1-4)
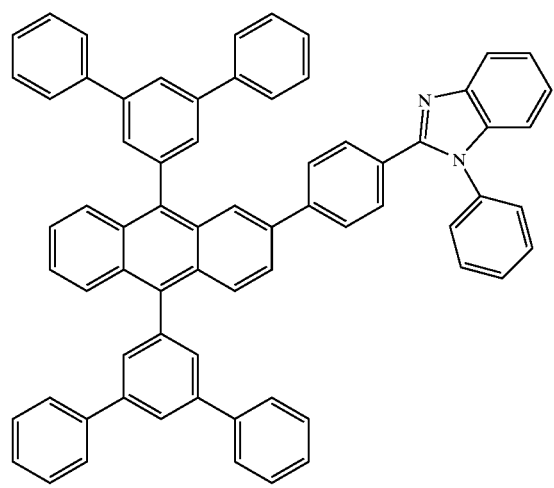 (1-5)

(1-6)
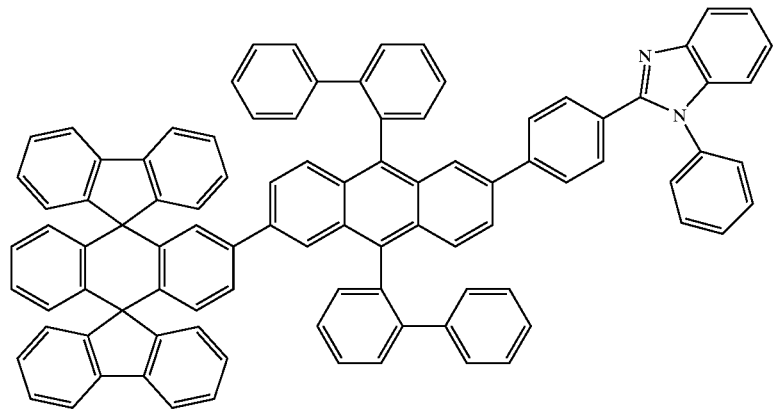
(1-7)
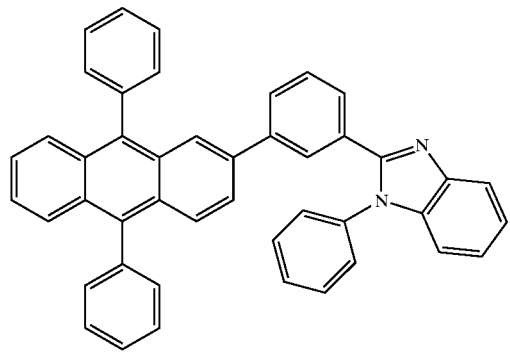
(1-8)
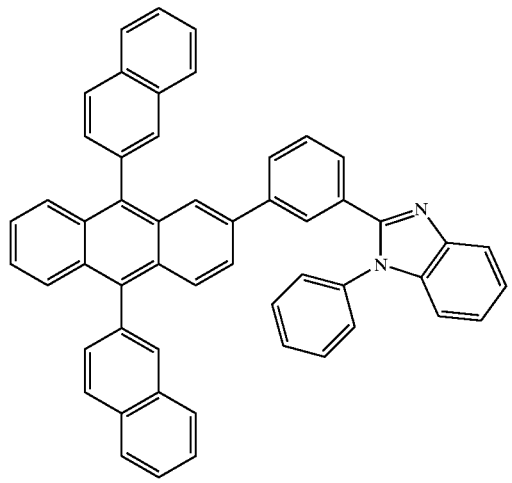
(1-9)
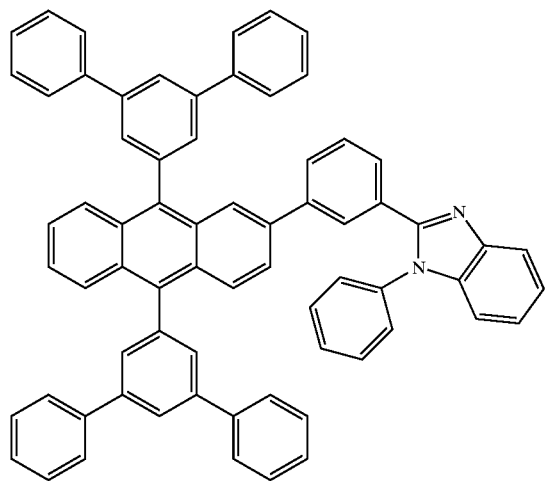
(1-10)
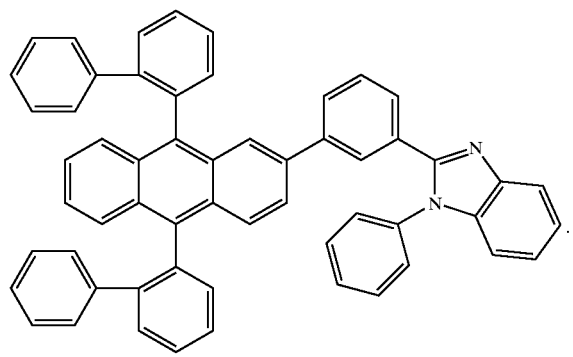

16. The organic electroluminescent display according to claim 6, wherein said display contains at least one compound represented by chemical formula 20, which is at least one selected from the group consisting of compounds of the following chemical formulas 2-1, 2-2, 2-3, 2-4 and 2-5:
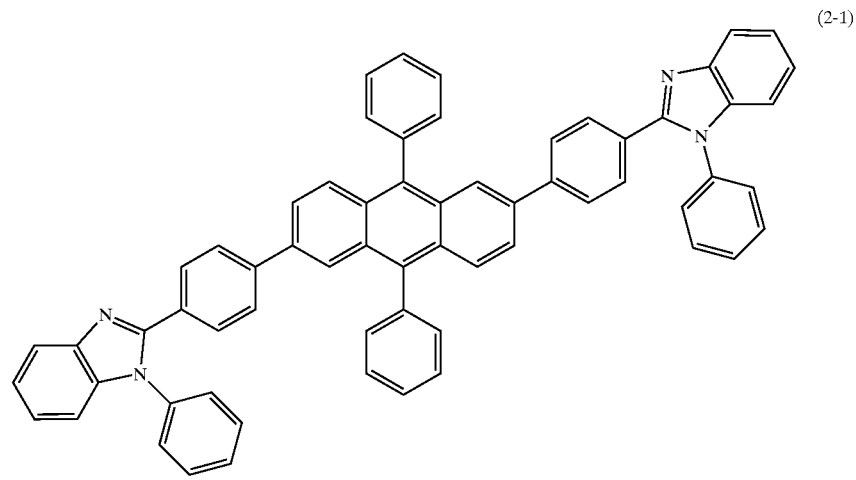
(2-1)
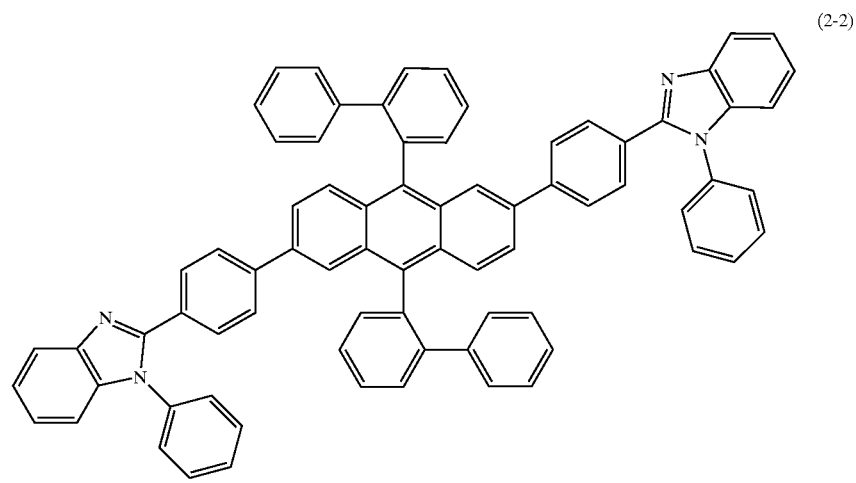
(2-2)
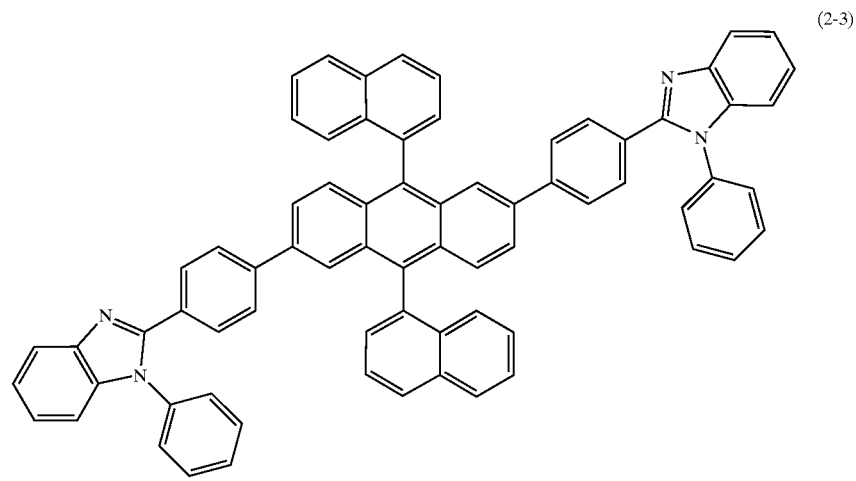
(2-3)

(2-4)
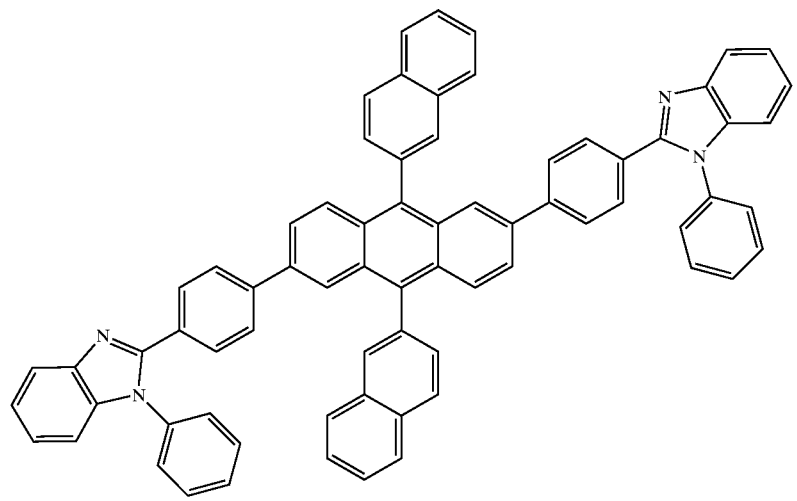
(2-5)
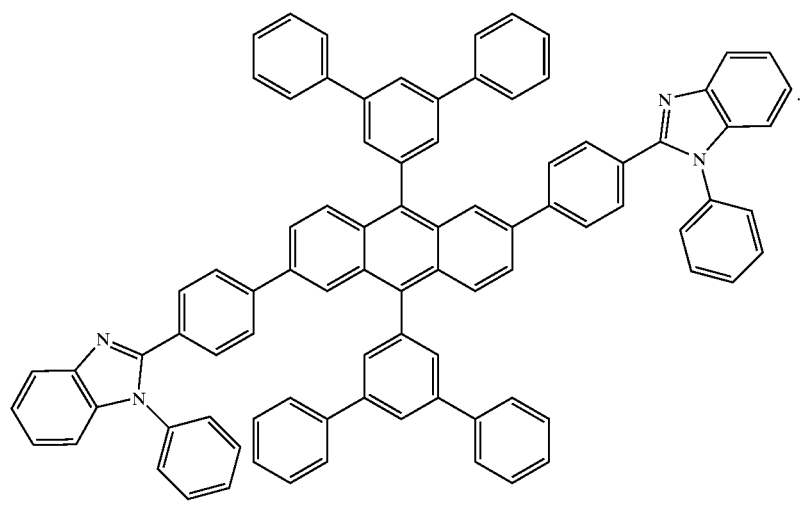
17. The organic electroluminescent display according to claim 6, wherein said display contains at least one compound represented by chemical formula 30, which is at least one selected from the group consisting of compounds of chemical formulas 3-1, 3-2, 3-3, 3-4 and 3-5:
(3-1)
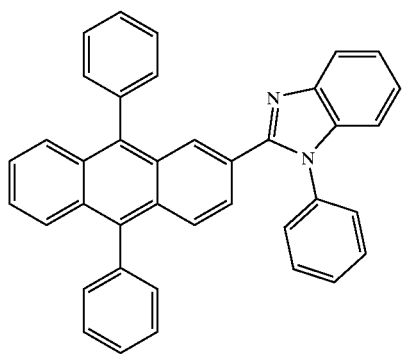
(3-2)
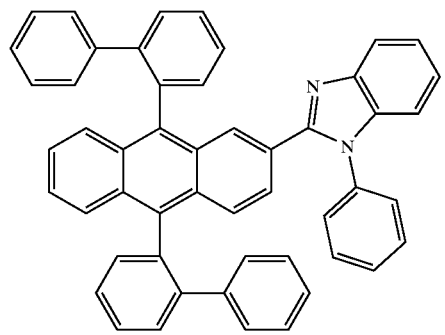

(3-3) 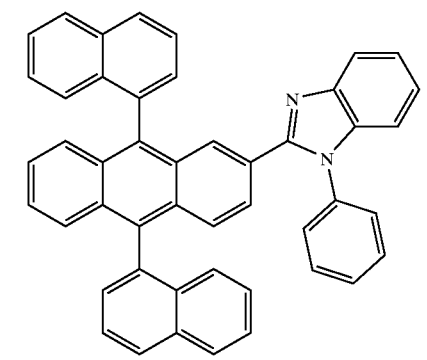
(4-1) 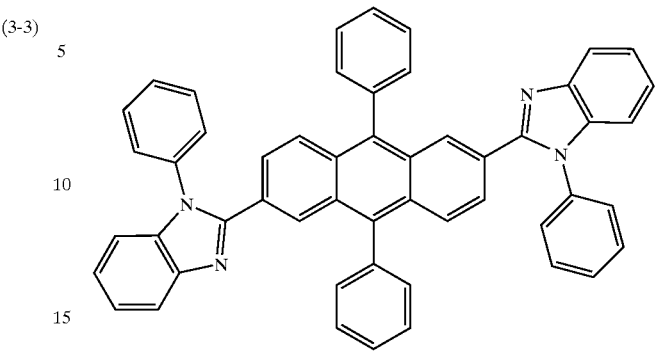
(3-4) 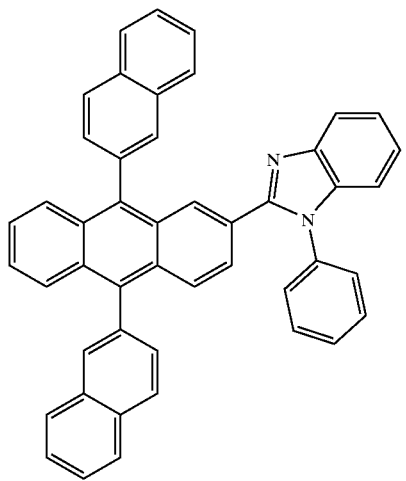
(4-2) 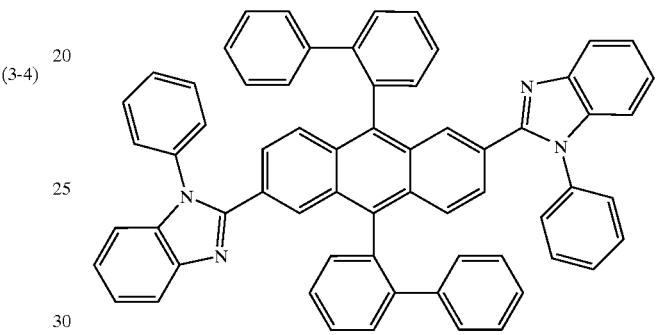
(4-3) 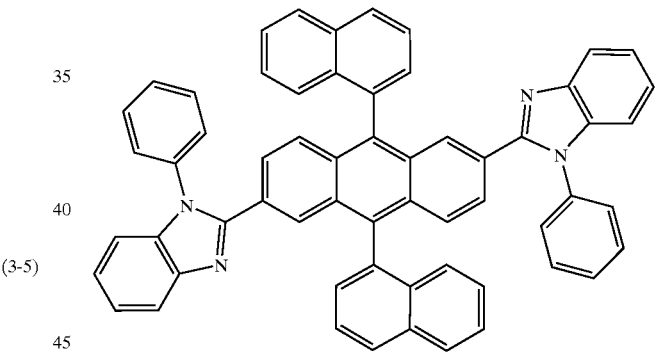
(3-5) 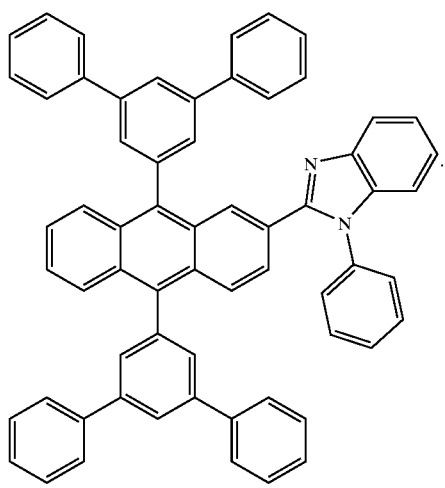
(4-4) 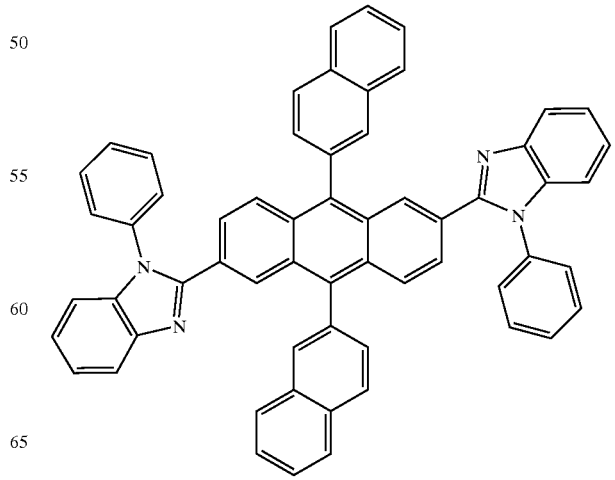
18. The organic electroluminescent display according to claim 6, wherein said display contains at least one compound represented by chemical formula 40, which is at least one selected from the group consisting of compounds of chemical formulas 4-1, 4-2, 4-3, 4-4 and 4-5:

-continued (4-5)

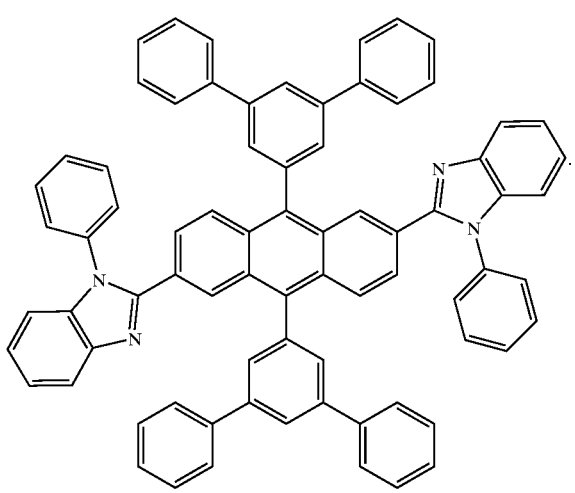

19. The organic electroluminescent display according to claim 6, wherein said display contains at least one compound represented by chemical formula 50, which is at least one selected from the group consisting of compounds of chemical formulae 5-1, 5-2, 5-3, 5-4 and 5-5:

(5-1)

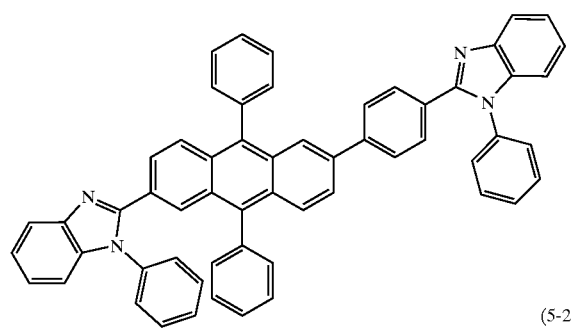

(5-2)

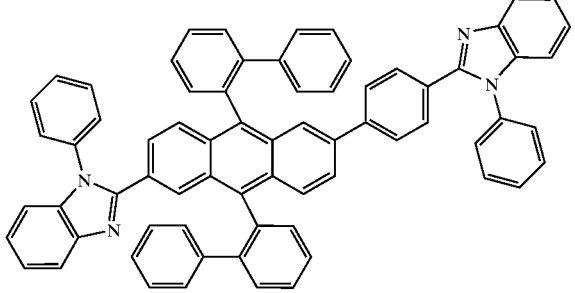

(5-3)

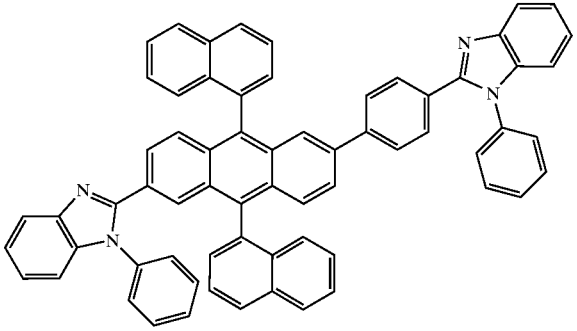

-continued (5-4)

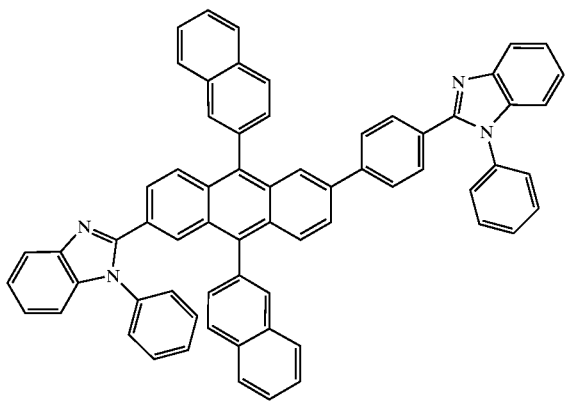

(5-5)

20. The compound according to claim 1, wherein where $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

21. The compound according to claim 2, wherein where $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

22. The compound according to claim 3, wherein $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

23. The compound according to claim 4, wherein $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

24. The compound according to claim 5, wherein $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

25. The organic electroluminescent display according to claim 6, wherein $R^5$ is $C_1$–$C_{20}$ alkyl or alkoxy aryl-substituted silicon groups, aryl-substituted boron groups, substituted or unsubstituted heterocyclic or aromatic groups, Cl, Br, F or I.

26. The compound according to claim 1, wherein $R^1$ and $R^2$ are independently or simultaneously phenyl, naphthyl, biphenyl, or anthracenyl;

Ar is phenylene, naphthylene, biphenylene, or anthracenylene;

$R^3$ is a hydrogen atom, a $C_{1-20}$ alkyl group or an aliphatic hydrocarbon, a substituted or unsubstituted phenyl, a substituted or unsubstituted naphthyl, a substituted or unsubstituted biphenyl, or a substituted or unsubstituted anthracenyl;

$R^4$ is a hydrogen atom, a $C_{1-12}$ alkyl or aliphatic hydrocarbon, phenyl, naphthyl, biphenyl, or anthracenyl; and $R^5$ is a hydrogen atom.

27. The compound according to claim 2, wherein $R^1$ and $R^2$ are independently or simultaneously phenyl, naphthyl, biphenyl, or anthracenyl;

Ar is phenylene, naphthylene, biphenylene, or anthracenylene;

$R^4$ is a hydrogen atom, a $C_{1-12}$ alkyl or aliphatic hydrocarbon, phenyl, naphthyl, biphenyl, or anthracenyl; and $R^5$ is a hydrogen atom.

28. The compound according to claim 3, wherein $R^1$ and $R^2$ are independently or simultaneously phenyl, naphthyl, biphenyl, or anthracenyl;

$R^3$ is a hydrogen atom, a $C_{1-20}$ alkyl group or an aliphatic hydrocarbon, a substituted or unsubstituted phenyl, a substituted or unsubstituted naphthyl, a substituted or unsubstituted biphenyl, or a substituted or unsubstituted anthracenyl;

$R^4$ is a hydrogen atom, a $C_{1-12}$ alkyl or aliphatic hydrocarbon, phenyl, naphthyl, biphenyl, or anthracenyl; and is a hydrogen atom.

29. The compound according to claim 4, wherein $R^1$ and $R^2$ are independently or simultaneously phenyl, naphthyl, biphenyl, or anthracenyl;

$R^4$ is a hydrogen atom, a $C_{1-12}$ alkyl or aliphatic hydrocarbon, phenyl, naphthyl, biphenyl, or anthracenyl; and $R^5$ is a hydrogen atom.

30. The compound according to claim 5, wherein $R^1$ and $R^2$ are independently or simultaneously phenyl, naphthyl, biphenyl, or anthracenyl;

Ar is phenylene, naphthylene, biphenylene, or anthracenylene;

$R^4$ is a hydrogen atom, a $C_{1-12}$ alkyl or aliphatic hydrocarbon, phenyl, naphthyl, biphenyl, or anthracenyl; and $R^5$ is a hydrogen atom.

31. The organic electroluminescent display according to claim 6, wherein in chemical formulas 1, 2, 3, 4, and 5, $R^1$ and $R^2$ are independently or simultaneously phenyl, naphthyl, biphenyl, or anthracenyl;

Ar is phenylene, naphthylene, biphenylene, or anthracenylene;

$R^3$ is a hydrogen atom, a $C_{1-20}$ alkyl group or an aliphatic hydrocarbon, a substituted or unsubstituted phenyl, a substituted or unsubstituted naphthyl, a substituted or unsubstituted biphenyl, or a substituted or unsubstituted anthracenyl;

$R^4$ is a hydrogen atom, a $C_{1-12}$ alkyl or aliphatic hydrocarbon, phenyl, naphthyl, biphenyl, or anthracenyl; and $R^5$ is a hydrogen atom.

32. The compound according to claim 1, wherein in $R^1$, $R^2$, Ar, $R^3$ and $R^4$, said aromatic ring is an aromatic heterocycle.

33. The compound according to claim 2, wherein in $R^1$, $R^2$, Ar, and $R^4$, said aromatic ring is an aromatic heterocycle.

34. The compound according to claim 3, wherein in $R^1$, $R^2$, $R^3$ and $R^4$, said aromatic ring is an aromatic heterocycle.

35. The compound according to claim 4, wherein in $R^1$, $R^2$, and $R^4$, said aromatic ring is an aromatic heterocycle.

36. The compound according to claim 5, wherein in $R^1$, $R^2$, Ar and $R^4$, said aromatic ring is an aromatic heterocycle.

37. The organic electroluminescent display according to claim 6, wherein in each of $R^1$, $R^2$, Ar, $R^3$ and $R^4$, said aromatic ring is an aromatic heterocycle.

* * * * *